(12) United States Patent
Shafer et al.

(10) Patent No.: US 8,661,573 B2
(45) Date of Patent: Mar. 4, 2014

(54) PROTECTIVE COVER FOR MEDICAL DEVICE HAVING ADHESIVE MECHANISM

(75) Inventors: Helen Zinreich Shafer, Owings Mills, MD (US); David Alan Zinreich, Owings Mills, MD (US); Douglas Crumb, Owings Mills, MD (US)

(73) Assignee: IZI Medical Products, Owings Mills, MD (US)

( * ) Notice: Subject to any disclaimer, the term of this patent is extended or adjusted under 35 U.S.C. 154(b) by 53 days.

(21) Appl. No.: 13/408,651

(22) Filed: Feb. 29, 2012

(65) Prior Publication Data

US 2013/0219601 A1  Aug. 29, 2013

(51) Int. Cl.
*A41D 13/00* (2006.01)

(52) U.S. Cl.
USPC .............................................. 2/468

(58) Field of Classification Search
USPC ......... 2/468, 171, 456, 171.2, 69, 207, 208.7, 2/209.13, 209.14, 202, 203, 204, 205, 2/209.4, DIG. 11, 195.1; 602/74, 75; 607/109, 139, 112
See application file for complete search history.

(56) References Cited

U.S. PATENT DOCUMENTS

| | | |
|---|---|---|
| 3,203,289 A | 8/1965 | Beekley |
| 3,354,467 A | 11/1967 | Beekley |
| 3,657,739 A * | 4/1972 | Holmes, Sr. .............. 2/468 |
| 3,941,127 A | 3/1976 | Froning |
| 4,126,126 A | 11/1978 | Bare et al. |
| D255,148 S | 5/1980 | Robinson et al. |
| 4,202,349 A | 5/1980 | Jones |
| 4,220,867 A | 9/1980 | Bloch, Jr. |
| 4,292,977 A | 10/1981 | Krause et al. |
| 4,326,534 A | 4/1982 | Axelgaard et al. |
| 4,365,634 A | 12/1982 | Bare et al. |
| 4,372,321 A | 2/1983 | Robinson |
| 4,377,869 A | 3/1983 | Venalainen et al. |
| 4,392,236 A | 7/1983 | Sandstrom et al. |
| 4,393,584 A | 7/1983 | Bare et al. |
| 4,401,356 A | 8/1983 | Bare |
| 4,416,286 A | 11/1983 | Iinuma et al. |
| 4,522,211 A | 6/1985 | Bare et al. |
| 4,676,776 A | 6/1987 | Howson |
| 4,702,256 A | 10/1987 | Robinson et al. |
| 4,722,733 A | 2/1988 | Howson |
| 4,733,661 A | 3/1988 | Palestrant |
| 4,734,674 A | 3/1988 | Thomas et al. |
| 4,795,437 A | 1/1989 | Schulte et al. |

(Continued)

FOREIGN PATENT DOCUMENTS

| | | |
|---|---|---|
| EP | 0941488 A1 | 9/1999 |
| EP | 0890117 B1 | 1/2002 |

(Continued)

*Primary Examiner* — Tejash Patel
(74) *Attorney, Agent, or Firm* — Alchemy-Partners, PC; Ajay A. Jagtiani

(57) ABSTRACT

A protective liner is described comprising a collar having a main collar portion, a first extension emanating from the main collar portion in a first direction, a second extension emanating from the main collar portion in a second direction opposite to the first direction. Disclosed embodiments may include a chest portion extending from the main collar portion. The protective liner may also include an adjustable releasable fastener for joining the first extension to the second extension. The adjustable releasable fastener may be disposed upon at least one of the first extension and second extension, wherein a material of the protective liner comprises a non-woven, fluid repellent material.

119 Claims, 19 Drawing Sheets

(56) References Cited

U.S. PATENT DOCUMENTS

| | | | |
|---|---|---|---|
| 4,804,054 A | 2/1989 | Howson et al. | |
| 4,810,243 A | 3/1989 | Howson | |
| 4,846,797 A | 7/1989 | Howson et al. | |
| 4,880,971 A | 11/1989 | Danisch | |
| 4,891,501 A * | 1/1990 | Lipton | 607/110 |
| 4,908,017 A | 3/1990 | Howson et al. | |
| 4,938,233 A | 7/1990 | Orrison, Jr. | |
| 4,950,255 A | 8/1990 | Brown et al. | |
| 4,964,855 A | 10/1990 | Todd et al. | |
| 4,981,142 A | 1/1991 | Dachman | |
| 5,054,480 A | 10/1991 | Bare et al. | |
| 5,056,523 A | 10/1991 | Hotchkiss, Jr. et al. | |
| 5,088,981 A | 2/1992 | Howson et al. | |
| 5,103,997 A | 4/1992 | Shillington et al. | |
| 5,184,720 A | 2/1993 | Packer et al. | |
| 5,197,476 A | 3/1993 | Nowacki et al. | |
| 5,198,877 A | 3/1993 | Schulz | |
| 5,232,452 A | 8/1993 | Russell et al. | |
| 5,249,581 A | 10/1993 | Horbal et al. | |
| 5,290,248 A | 3/1994 | Bierman et al. | |
| 5,295,483 A | 3/1994 | Nowacki et al. | |
| 5,306,271 A | 4/1994 | Zinreich et al. | |
| 5,314,411 A | 5/1994 | Bierman et al. | |
| 5,321,257 A | 6/1994 | Danisch | |
| 5,365,952 A | 11/1994 | Noble et al. | |
| 5,368,030 A | 11/1994 | Zinreich et al. | |
| 5,383,234 A | 1/1995 | Russell | |
| 5,407,440 A | 4/1995 | Zinreich et al. | |
| 5,427,099 A | 6/1995 | Adams | |
| 5,435,066 A | 7/1995 | Bare et al. | |
| 5,458,628 A * | 10/1995 | Cipolla | 607/112 |
| 5,469,847 A | 11/1995 | Zinreich et al. | |
| 5,474,569 A | 12/1995 | Zinreich et al. | |
| 5,475,451 A | 12/1995 | Robert et al. | |
| 5,523,581 A | 6/1996 | Cadwalader et al. | |
| 5,545,993 A | 8/1996 | Taguchi et al. | |
| 5,577,995 A | 11/1996 | Walker et al. | |
| 5,609,827 A | 3/1997 | Russell et al. | |
| 5,628,733 A | 5/1997 | Zinreich et al. | |
| 5,633,494 A | 5/1997 | Danisch | |
| 5,665,653 A | 9/1997 | Bare et al. | |
| 5,702,128 A | 12/1997 | Maxim et al. | |
| 5,714,105 A | 2/1998 | Gysin et al. | |
| 5,743,899 A | 4/1998 | Zinreich | |
| RE35,816 E | 6/1998 | Schulz | |
| 5,772,642 A | 6/1998 | Ciamacco, Jr. et al. | |
| 5,795,335 A | 8/1998 | Zinreich | |
| 5,806,515 A | 9/1998 | Bare et al. | |
| 5,817,105 A | 10/1998 | Van Der Brug | |
| 5,827,202 A | 10/1998 | Miraki et al. | |
| 5,828,770 A | 10/1998 | Leis et al. | |
| 5,833,682 A | 11/1998 | Amplatz et al. | |
| 5,841,830 A | 11/1998 | Barni et al. | |
| 5,848,125 A | 12/1998 | Arnett | |
| 5,887,437 A | 3/1999 | Maxim | |
| 5,908,410 A | 6/1999 | Weber et al. | |
| 5,923,417 A | 7/1999 | Leis | |
| 5,947,950 A | 9/1999 | Shillington et al. | |
| 5,954,648 A | 9/1999 | Van Der Brug | |
| 5,967,982 A | 10/1999 | Barnett | |
| 5,989,182 A | 11/1999 | Hori et al. | |
| RE36,461 E | 12/1999 | Russell et al. | |
| 6,013,087 A | 1/2000 | Adams et al. | |
| 6,024,216 A | 2/2000 | Shillington et al. | |
| 6,041,094 A | 3/2000 | Russell | |
| 6,045,565 A | 4/2000 | Ellis et al. | |
| D424,530 S | 5/2000 | Kurtz et al. | |
| 6,059,718 A | 5/2000 | Taniguchi et al. | |
| 6,061,644 A | 5/2000 | Leis | |
| 6,127,672 A | 10/2000 | Danisch | |
| 6,179,860 B1 | 1/2001 | Fulton, III et al. | |
| 6,264,599 B1 | 7/2001 | Slater et al. | |
| 6,268,605 B1 | 7/2001 | Orava et al. | |
| 6,269,148 B1 | 7/2001 | Jessop et al. | |
| D447,567 S | 9/2001 | Murphy et al. | |
| 6,288,785 B1 | 9/2001 | Frantz et al. | |
| 6,300,138 B1 | 10/2001 | Gleason et al. | |
| 6,302,870 B1 | 10/2001 | Jacobsen et al. | |
| 6,379,319 B1 | 4/2002 | Garibotto et al. | |
| 6,385,482 B1 | 5/2002 | Boksberger et al. | |
| 6,422,048 B1 | 7/2002 | Fontes et al. | |
| 6,485,465 B2 | 11/2002 | Moberg et al. | |
| 6,490,473 B1 | 12/2002 | Katznelson et al. | |
| 6,494,835 B1 | 12/2002 | Ciezki et al. | |
| 6,537,205 B1 | 3/2003 | Smith | |
| 6,553,326 B1 | 4/2003 | Kirsch et al. | |
| 6,554,848 B2 | 4/2003 | Boylan et al. | |
| 6,582,417 B1 | 6/2003 | Ledesma et al. | |
| 6,625,563 B2 | 9/2003 | Kirsch et al. | |
| 6,626,445 B2 | 9/2003 | Murphy et al. | |
| 6,659,980 B2 | 12/2003 | Moberg et al. | |
| 6,676,610 B2 | 1/2004 | Morton et al. | |
| 6,685,644 B2 | 2/2004 | Seo et al. | |
| 6,685,666 B1 | 2/2004 | Fontenot | |
| 6,689,142 B1 | 2/2004 | Tremaglio, Jr. et al. | |
| 6,712,785 B2 | 3/2004 | Morton et al. | |
| 6,714,628 B2 | 3/2004 | Broyles et al. | |
| 6,782,289 B1 | 8/2004 | Strauss | |
| 6,826,257 B2 | 11/2004 | Sayre et al. | |
| 6,836,745 B2 | 12/2004 | Seiler et al. | |
| 6,845,271 B2 | 1/2005 | Fang et al. | |
| D503,980 S | 4/2005 | Sayre et al. | |
| 6,875,184 B2 | 4/2005 | Morton et al. | |
| 6,899,696 B2 | 5/2005 | Morton et al. | |
| 6,903,307 B1 | 6/2005 | McConnell et al. | |
| 6,907,293 B2 | 6/2005 | Grill et al. | |
| D510,169 S | 9/2005 | Deane et al. | |
| 6,981,950 B2 | 1/2006 | Morton et al. | |
| 6,985,558 B1 | 1/2006 | Russell | |
| 6,990,427 B2 | 1/2006 | Kirsch et al. | |
| 7,047,078 B2 | 5/2006 | Boggs, II et al. | |
| 7,066,985 B2 | 6/2006 | Deane et al. | |
| D528,212 S | 9/2006 | Conway et al. | |
| 7,120,499 B2 | 10/2006 | Thrope et al. | |
| 7,127,040 B2 | 10/2006 | Sayre et al. | |
| 7,135,059 B2 | 11/2006 | Deane et al. | |
| 7,137,712 B2 | 11/2006 | Brunner et al. | |
| 7,140,769 B2 | 11/2006 | Kay | |
| 7,194,296 B2 | 3/2007 | Frantz et al. | |
| D539,530 S | 4/2007 | Sanderson et al. | |
| 7,204,796 B1 | 4/2007 | Seiler | |
| 7,206,626 B2 | 4/2007 | Quaid, III | |
| D545,660 S | 7/2007 | Robinson et al. | |
| D547,048 S | 7/2007 | Conway et al. | |
| 7,239,918 B2 | 7/2007 | Strother et al. | |
| 7,245,958 B1 | 7/2007 | Navab et al. | |
| 7,263,159 B2 | 8/2007 | Russell | |
| D552,735 S | 10/2007 | Archambault | |
| 7,283,867 B2 | 10/2007 | Strother et al. | |
| D559,985 S | 1/2008 | Dzierlatka | |
| D559,987 S | 1/2008 | Strother et al. | |
| 7,341,841 B2 | 3/2008 | Metzger et al. | |
| 7,343,202 B2 | 3/2008 | Mrva et al. | |
| 7,346,417 B2 | 3/2008 | Luth et al. | |
| 7,353,125 B2 | 4/2008 | Nieminen et al. | |
| 7,364,553 B2 | 4/2008 | Paz et al. | |
| 7,376,467 B2 | 5/2008 | Thrope et al. | |
| 7,438,745 B2 | 10/2008 | Deane et al. | |
| D581,530 S | 11/2008 | Thierfelder et al. | |
| 7,457,443 B2 | 11/2008 | Persky | |
| 7,465,847 B2 | 12/2008 | Fabian | |
| 7,468,043 B2 | 12/2008 | Morton et al. | |
| 7,469,187 B2 | 12/2008 | Nieminen et al. | |
| 7,491,198 B2 | 2/2009 | Kockro | |
| 7,496,222 B2 | 2/2009 | Mussack et al. | |
| D590,948 S | 4/2009 | Archambault | |
| D590,949 S | 4/2009 | Broyles | |
| 7,529,387 B2 | 5/2009 | Kotake et al. | |
| 7,549,960 B2 | 6/2009 | Govari | |
| 7,565,198 B2 | 7/2009 | Bennett et al. | |
| 7,571,000 B2 | 8/2009 | Boggs, II et al. | |
| 7,571,002 B2 | 8/2009 | Thrope et al. | |
| 7,575,557 B2 | 8/2009 | Morton et al. | |
| 7,577,474 B2 | 8/2009 | Vilsmeier | |

(56) References Cited

U.S. PATENT DOCUMENTS

| | | |
|---|---|---|
| D602,590 S | 10/2009 | Dzierlatka |
| 7,617,932 B2 | 11/2009 | Windus-Smith et al. |
| 7,623,925 B2 | 11/2009 | Grill et al. |
| 7,627,137 B2 | 12/2009 | Takemoto |
| 7,637,913 B2 | 12/2009 | De Villiers et al. |
| 7,651,506 B2 | 1/2010 | Bova et al. |
| D609,255 S | 2/2010 | Bare et al. |
| D610,261 S | 2/2010 | Strother et al. |
| 7,687,239 B2 | 3/2010 | Goldberg et al. |
| 7,696,876 B2 | 4/2010 | Dimmer et al. |
| 7,696,899 B2 | 4/2010 | Immerz et al. |
| 7,706,600 B2 | 4/2010 | Kreeger et al. |
| 7,729,475 B2 | 6/2010 | Kito et al. |
| 7,730,887 B2 | 6/2010 | Deane et al. |
| D619,728 S | 7/2010 | Bare et al. |
| 7,758,541 B2 | 7/2010 | Wallace et al. |
| 7,760,909 B2 | 7/2010 | Manus |
| 7,761,167 B2 | 7/2010 | Bennett et al. |
| 7,763,030 B2 | 7/2010 | Blau et al. |
| 7,771,339 B2 | 8/2010 | Isacsson et al. |
| 7,781,041 B2 | 8/2010 | Broyles |
| 7,783,441 B2 | 8/2010 | Nieminen et al. |
| 7,794,469 B2 | 9/2010 | Kao et al. |
| 7,797,058 B2 | 9/2010 | Mrva et al. |
| D625,345 S | 10/2010 | Bare et al. |
| D625,428 S | 10/2010 | Bare et al. |
| 7,806,858 B2 | 10/2010 | Smith et al. |
| 7,809,184 B2 | 10/2010 | Neubauer et al. |
| 7,813,809 B2 | 10/2010 | Strother et al. |
| 7,820,446 B2 | 10/2010 | Feilkas et al. |
| D627,469 S | 11/2010 | Dzierlatka |
| D631,547 S | 1/2011 | Sayre et al. |
| 7,861,326 B2 * | 1/2011 | Harty ................................ 2/468 |
| 7,865,236 B2 | 1/2011 | Cory et al. |
| 7,865,250 B2 | 1/2011 | Mrva et al. |
| 7,874,686 B2 | 1/2011 | Rossner et al. |
| 7,878,981 B2 | 2/2011 | Strother et al. |
| 7,883,545 B2 | 2/2011 | Tuma |
| 7,894,913 B2 | 2/2011 | Boggs et al. |
| 7,896,815 B2 | 3/2011 | Thrope et al. |
| 7,922,391 B2 | 4/2011 | Essenreiter et al. |
| 7,922,731 B2 | 4/2011 | Schumacher et al. |
| 7,945,311 B2 | 5/2011 | McCloy et al. |
| 7,957,925 B2 | 6/2011 | Nieminen et al. |
| 7,962,189 B2 | 6/2011 | Numada et al. |
| 7,972,300 B2 | 7/2011 | Smith et al. |
| 7,983,739 B2 | 7/2011 | Dunki-Jacobs et al. |
| D643,928 S | 8/2011 | Dzierlatka |
| 7,996,092 B2 | 8/2011 | Mrva et al. |
| 8,012,295 B1 | 9/2011 | Broyles |
| 8,023,712 B2 | 9/2011 | Ikuma et al. |
| 8,051,856 B2 | 11/2011 | Bare et al. |
| 8,052,649 B2 | 11/2011 | Wright |
| 8,071,319 B2 | 12/2011 | Metzger et al. |
| 8,083,759 B2 | 12/2011 | Cox et al. |
| 8,088,104 B2 | 1/2012 | Smith et al. |
| 8,090,428 B2 | 1/2012 | De Villiers et al. |
| 8,104,958 B2 | 1/2012 | Weiser et al. |
| 8,126,530 B2 | 2/2012 | Bare et al. |
| 8,126,535 B2 | 2/2012 | Maier et al. |
| 8,128,576 B2 | 3/2012 | Tracey et al. |
| 2004/0243146 A1 | 12/2004 | Chesbrough et al. |
| 2005/0112758 A1 | 5/2005 | Archambault et al. |
| 2005/0211930 A1 | 9/2005 | Demeo et al. |
| 2005/0228410 A1 | 10/2005 | Berreklouw |
| 2005/0284982 A1 | 12/2005 | Kasper |
| 2006/0063973 A1 | 3/2006 | Makower et al. |
| 2006/0149345 A1 | 7/2006 | Boggs, II et al. |
| 2006/0173356 A1 | 8/2006 | Feilkas |
| 2006/0200178 A1 | 9/2006 | Hamel et al. |
| 2006/0200219 A1 | 9/2006 | Thrope et al. |
| 2007/0060968 A1 | 3/2007 | Strother et al. |
| 2007/0060980 A1 | 3/2007 | Strother et al. |
| 2007/0066995 A1 | 3/2007 | Strother et al. |
| 2007/0093709 A1 | 4/2007 | Abernathie |
| 2007/0238983 A1 | 10/2007 | Suthanthiran et al. |
| 2007/0239224 A1 | 10/2007 | Bennett et al. |
| 2007/0255212 A1 | 11/2007 | Smith et al. |
| 2007/0270921 A1 | 11/2007 | Strother et al. |
| 2007/0293910 A1 | 12/2007 | Strother et al. |
| 2008/0033500 A1 | 2/2008 | Strother et al. |
| 2008/0039866 A1 | 2/2008 | Stetz et al. |
| 2008/0065171 A1 | 3/2008 | Fang et al. |
| 2008/0071322 A1 | 3/2008 | Mrva et al. |
| 2008/0091224 A1 | 4/2008 | Griffis, III et al. |
| 2008/0091266 A1 | 4/2008 | Griffis, III et al. |
| 2008/0107305 A1 | 5/2008 | Vanderkooy et al. |
| 2008/0132969 A1 | 6/2008 | Bennett et al. |
| 2008/0132974 A1 | 6/2008 | Strother et al. |
| 2008/0139916 A1 | 6/2008 | Maier et al. |
| 2008/0146942 A1 | 6/2008 | Dala-Krishna |
| 2008/0161874 A1 | 7/2008 | Bennett et al. |
| 2008/0172119 A1 | 7/2008 | Yamasaki et al. |
| 2008/0177351 A1 | 7/2008 | Fang et al. |
| 2008/0200844 A1 | 8/2008 | Millahn et al. |
| 2008/0249397 A1 | 10/2008 | Kapadia |
| 2008/0281989 A1 | 11/2008 | Hager et al. |
| 2008/0287782 A1 | 11/2008 | Traboulsi et al. |
| 2008/0306379 A1 | 12/2008 | Ikuma et al. |
| 2008/0312673 A1 | 12/2008 | Visanathan et al. |
| 2009/0030380 A1 | 1/2009 | Binmoeller |
| 2009/0036775 A1 | 2/2009 | Ikuma et al. |
| 2009/0087380 A1 | 4/2009 | Fasching et al. |
| 2009/0126088 A1 | 5/2009 | Yadav et al. |
| 2009/0132018 A1 | 5/2009 | DiUbaldi et al. |
| 2009/0171324 A1 | 7/2009 | Chong et al. |
| 2009/0216116 A1 | 8/2009 | Roger |
| 2009/0259126 A1 | 10/2009 | Saal et al. |
| 2009/0281421 A1 | 11/2009 | Culp et al. |
| 2009/0287467 A1 | 11/2009 | Sparks et al. |
| 2009/0289182 A1 | 11/2009 | Pavsner |
| 2009/0299416 A1 | 12/2009 | Hanni et al. |
| 2009/0305315 A1 | 12/2009 | Gandola et al. |
| 2010/0036445 A1 | 2/2010 | Sakai et al. |
| 2010/0036454 A1 | 2/2010 | Bennett et al. |
| 2010/0070069 A1 | 3/2010 | Hofstadler et al. |
| 2010/0075430 A1 | 3/2010 | Hofstadler et al. |
| 2010/0076455 A1 | 3/2010 | Birkenbach et al. |
| 2010/0100081 A1 | 4/2010 | Tuma et al. |
| 2010/0113860 A1 | 5/2010 | Traboulsi et al. |
| 2010/0113912 A1 | 5/2010 | Traboulsi et al. |
| 2010/0128558 A1 | 5/2010 | Hofstadler et al. |
| 2010/0136570 A1 | 6/2010 | Goldberg et al. |
| 2010/0137857 A1 | 6/2010 | Shroff et al. |
| 2010/0152808 A1 | 6/2010 | Boggs, II |
| 2010/0152809 A1 | 6/2010 | Boggs, II |
| 2010/0158869 A1 | 6/2010 | Kaemmerer |
| 2010/0191114 A1 | 7/2010 | Hyun et al. |
| 2010/0219336 A1 | 9/2010 | Hofstadler et al. |
| 2010/0268151 A1 | 10/2010 | Mauge et al. |
| 2010/0274310 A1 | 10/2010 | Boggs, II et al. |
| 2010/0312247 A1 | 12/2010 | Tuma |
| 2010/0324484 A1 | 12/2010 | Smith et al. |
| 2011/0014027 A1 | 1/2011 | Drader et al. |
| 2011/0029071 A1 | 2/2011 | Zlotnick et al. |
| 2011/0051892 A1 | 3/2011 | Shafer |
| 2011/0077628 A1 | 3/2011 | Hoey et al. |
| 2011/0086114 A1 | 4/2011 | Zinreich et al. |
| 2011/0093032 A1 | 4/2011 | Boggs, II et al. |
| 2011/0118627 A1 | 5/2011 | Morton et al. |
| 2011/0152600 A1 | 6/2011 | Scott et al. |
| 2011/0166417 A1 | 7/2011 | Lin |
| 2011/0224537 A1 | 9/2011 | Brunner |
| 2011/0230906 A1 | 9/2011 | Modesitt et al. |

FOREIGN PATENT DOCUMENTS

| | | |
|---|---|---|
| EP | 1244394 B1 | 10/2002 |
| EP | 1251778 B1 | 10/2002 |
| EP | 1272862 B1 | 1/2003 |
| EP | 0847253 B1 | 3/2003 |
| EP | 1303771 B1 | 4/2003 |
| EP | 1330183 A2 | 7/2003 |
| EP | 1034440 B1 | 10/2003 |

(56) References Cited

FOREIGN PATENT DOCUMENTS

| | | |
|---|---|---|
| EP | 1158924 B1 | 3/2004 |
| EP | 1399765 B1 | 3/2004 |
| EP | 0836438 B1 | 9/2004 |
| EP | 1535021 A2 | 6/2005 |
| EP | 1613213 A1 | 1/2006 |
| EP | 1698373 B1 | 9/2006 |
| EP | 1720606 B1 | 11/2006 |
| EP | 1096268 B1 | 12/2006 |
| EP | 1761303 A4 | 3/2007 |
| EP | 1786511 A4 | 5/2007 |
| EP | 1865342 A3 | 12/2007 |
| EP | 1885438 A1 | 2/2008 |
| EP | 1993440 A2 | 11/2008 |
| EP | 2024018 A4 | 2/2009 |
| EP | 2092899 A2 | 8/2009 |
| EP | 2106273 A2 | 10/2009 |
| EP | 2269507 A1 | 1/2011 |
| EP | 2052681 A3 | 2/2011 |
| EP | 2318088 A1 | 5/2011 |
| JP | 07-216606 A | 8/1995 |
| WO | WO 89/00831 A1 | 2/1989 |

* cited by examiner

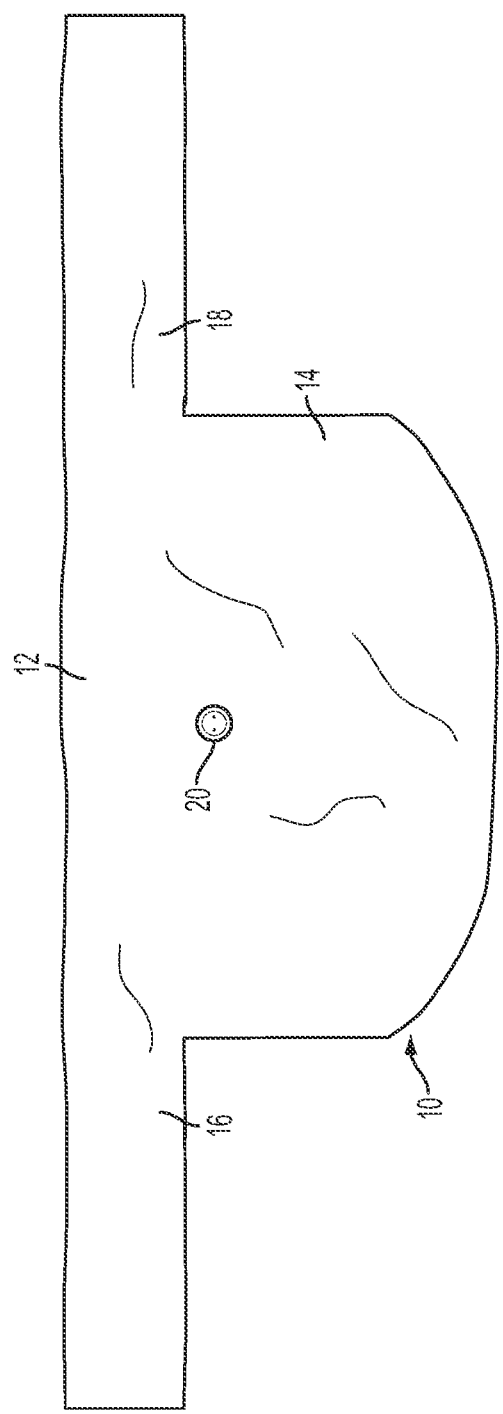

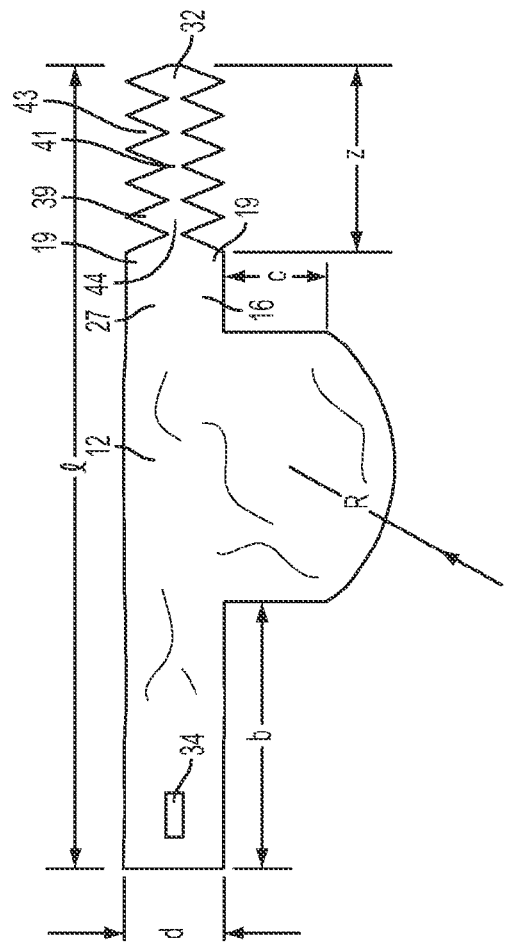
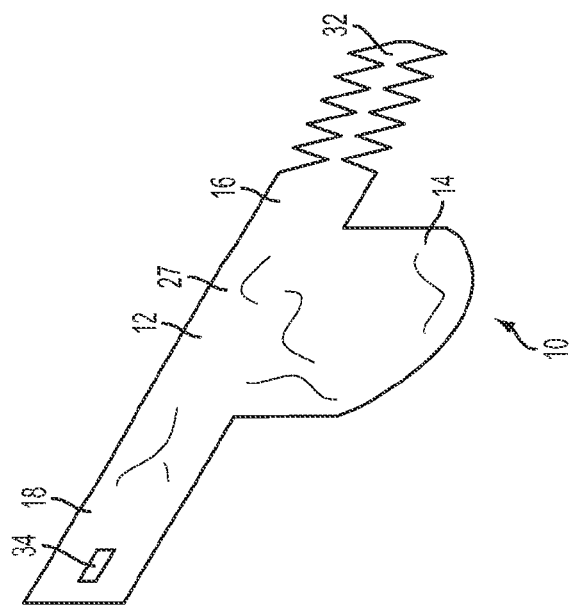
FIG. 7B
FIG. 7A

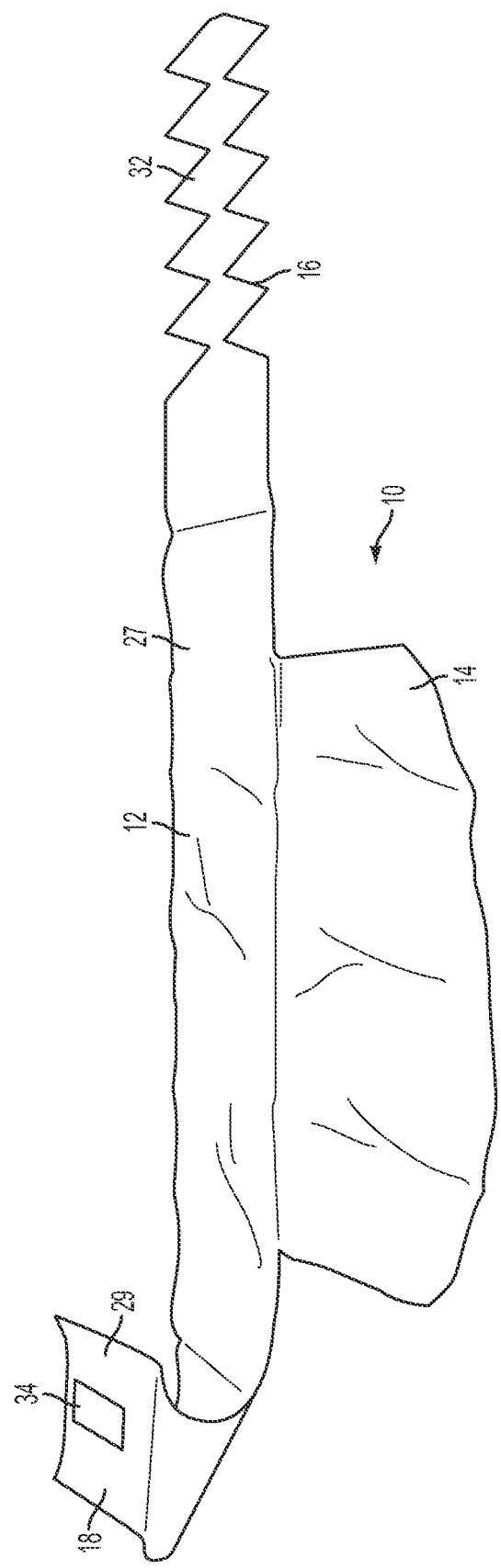

PROTECTIVE COVER FOR MEDICAL DEVICE HAVING ADHESIVE MECHANISM

CROSS-REFERENCE TO RELATED APPLICATIONS

This application makes reference to the following applications filed Feb. 29, 2011 to the same inventors as the present application: application Ser. No. 13/408,582 entitled "PROTECTIVE COVER FOR MEDICAL DEVICE," application Ser. No. 13/408,699 entitled "PROTECTIVE COVER FOR MEDICAL DEVICE HAVING A RADIATION DETECTOR" and application Ser. No. 13/408,766 entitled "PROTECTIVE COVER FOR MEDICAL DEVICE HAVING ETCHED FASTENERS" the entire content and disclosures of which are incorporated herein by reference in their entirety.

BACKGROUND

1. Field of the Invention

The present invention relates generally to protective apparel employed as a barrier to prevent contamination of worn shielding attire. More particularly, it relates to a liner for averting transfer of bodily fluids from a patient and contamination of a radiation shield during radiological procedures.

2. Related Art

Radiological technologists often utilize lead apparel for protection against X-rays needed during X-ray procedures. Dentists may also use lead apparel for the protection for their patients during dental X-ray examinations. It is estimated that upwards of 40 million mammography procedures are conducted annually in the United States; upwards of 100 million dental X-rays are estimated to be performed annually in the United States. Concerns exist for having to use a thyroid shield previously used by an undetermined number of people. Lead protective gear is expensive and therefore used over frequently by personnel and patients, which may cause it to become soiled and stained in the process.

In general, radiation shields which cover portions of the body, such as the thyroid area, are known in the art. Examples of such radiation shields are described in U.S. Pat. No. 4,938,233, filed by Orrison, Jr., issued Jul. 3, 1990, entitled "Radiation Shield." These radiation shields are generally comprised of a body of radiation-attenuating material and an attachment member. The attachment member of the radiation shield is configured to be worn around an appendage such as the neck so that the radiation-attenuating material protects a particular body portion.

Radiation shields are intended for use in non-sterile environments during radiological diagnostic procedures or oncological treatments. The shields are worn, for example, by patients to selectively isolate, shroud and protect particular regions of the anatomy. Many radiation shields are designed to be reusable. Thus, the same radiation shield may be worn, perhaps, hundreds of times by different patients. As such, during usage, the radiation shield may become exposed, for example, to sweat and other fluids from a patient during radiological processes such as during mammograms and/or dental X-rays. It is, therefore, necessary to clean the radiation shield between patient uses. The cleaning and disinfecting process may reduce the efficiency of the office practice due to the fact that the aforementioned cleaning process can take a considerable amount of time and effort to perform by office personnel. In addition, the cleaning process would most likely need to be performed multiple times throughout the day to serve multiple patients.

Nevertheless, despite cleaning efforts, the radiation shields often become soiled with bodily fluids or otherwise-unsightly discolorations. These stained radiation shields, which often contain environmentally unfriendly materials, must, therefore, be disposed of In addition, these events may pose a barrier against green efforts as the discarded radiation shields may eventually accumulate in landfills. Further, if the radiation shield is not properly cleaned, the patient or practitioner may unknowingly wear a soiled or otherwise unsanitary shield.

Another consideration raised during radiological procedures is knowing whether undesired body portions have been exposed to radiation. There are currently no conventional systems employed within shielding equipment to indicate whether localized body portions have been exposed during X-ray procedures in a medical office or dental office environment.

Attempts have been made, within the prior art, to address shielding radiation shields from direct contact with a user. For example, U.S. Pat. No. 5,523,581, filed by Cadwalader, issued Jun. 4, 1996, entitled "Slipcover for Radiation Shields" provides a slipcover or covering for containing a flexible radiation shield that allows the radiation shield to be reused without experiencing staining. However, the intricate design of the slipcover may make its application cumbersome during usage as one attempts to insert the flexible radiation shield within its pocket to secure it therein. Furthermore, the process of removing and employing another slipcover between patient use is time consuming and may also inadvertently expose the radiation shield to contact with soiled regions of the slipcover as it is removed.

Thus, there is a need for allowing radiation shields to be hygienically reused and for eliminating cleaning and disinfecting of the radiation shield between patient use. There is also a need for providing a low cost, disposable and easily employed solution for shielding transfer of bodily fluids to the radiation shield. A need also exists for providing an indicator to alert a user to radiation exposure to particular areas of the body.

SUMMARY OF THE INVENTION

It is, therefore, an object of the present invention to overcome the deficiencies of the prior art to include a disclosed exemplary embodiment that, in some embodiments, includes a protective liner comprising: a collar having a main collar portion, a first extension emanating from the main collar portion in a first direction, a second extension emanating from the main collar portion in a second direction opposite to the first direction. Disclosed embodiments may include a chest portion extending from the main collar portion. The protective liner may also include an adjustable releasable fastener for joining the first extension to the second extension. The adjustable releasable fastener may be disposed upon at least one of the first extension and second extension, wherein a material of the protective liner comprises a non-woven, fluid repellent material.

In accordance with another embodiment of the present invention, a protective liner is provided comprising: a first material forming a collar having a main collar portion, a first extension emanating from the main collar portion in a first direction, and a second extension emanating from the main collar portion in a second direction opposite to the first direction. Disclosed embodiments may include a chest portion extending from the main collar portion. The protective line may also include an adjustable releasable fastener for joining the first extension to the second extension. The adjustable releasable fastener may be disposed upon at least one of the first extension and second extension, wherein a material of the protective liner comprises a non-woven material. A second material coating a surface of the first material may be provided, wherein the second material is fluid repellent.

In yet another embodiment of the present invention, a protective liner is provided comprising: a collar having a main collar portion, a first extension emanating from the main collar portion in a first direction, a second extension emanating from the main collar portion in a second direction opposite to the first direction, a first tie extension extending from the first extension and a second tie extension extending from the second extension. Embodiments may provide a chest portion extending from the main collar portion, wherein a material of the protective liner comprises a non-woven, fluid repellent material.

In still another embodiment of the present invention, a protective liner is provided comprising: a first material forming a collar having a main collar portion, a first extension emanating from the main collar portion in a first direction and a second extension emanating from the main collar portion in a second direction opposite to the first direction. The protective liner may provide a first tie extension extending from the first extension and a second tie extension extending from the second extension. A chest portion may be provided extending from the main collar portion, wherein a material of the protective liner comprises a non-woven material. Embodiments may provide a second material coating a surface of the first material, wherein the second material is fluid repellent.

In another embodiment of the present invention, a protective liner is provided comprising: a collar comprising: a main collar portion, a first extension emanating from the main collar portion in a first direction, a second extension emanating from the main collar portion in a second direction opposite to the first direction, a chest portion extending from the main collar portion, an adjustable releasable fastener for joining the first extension to the second extension, the adjustable releasable fastener disposed upon at least one of the first extension and second extension, wherein a material of the protective liner comprises a non-woven, fluid repellent material, wherein the adjustable releasable fastener comprises fastener portions formed from a surface of the first extension and a slot formed in the second extension for receiving the fastener portions.

In still another embodiment of the present invention, a protective liner is provided comprising: a collar comprising: a main collar portion, a first extension emanating from the main collar portion in a first direction, a second extension emanating from the main collar portion in a second direction opposite to the first direction, a chest portion extending from the main collar portion, an adjustable releasable fastener for joining the first extension to the second extension, the adjustable releasable fastener disposed upon at least one of the first extension and second extension, wherein a material of the protective liner comprises a non-woven, fluid repellent material, and a radiation device attached to the material.

In another embodiment of the present invention, a protective liner is provided comprising: a first material forming a collar comprising a main collar portion, a first extension emanating from the main collar portion in a first direction, a second extension emanating from the main collar portion in a second direction opposite to the first direction, a chest portion extending from the main collar portion, an adjustable releasable fastener for joining the first extension to the second extension, the adjustable releasable fastener disposed upon at least one of the first extension and second extension, wherein a material of the protective liner comprises a non-woven material, a second material coating a surface of the first material, wherein the second material is fluid repellent, and a radiation device attached to the first material.

In still another embodiment of the present invention, a protective liner is provided comprising: a collar comprising: a collar comprising a main collar portion, a first extension emanating from the main collar portion in a first direction, a second extension emanating from the main collar portion in a second direction opposite to the first direction, a first tie extension extending from the first extension, a second tie extension extending from the second extension, a chest portion extending from the main collar portion, wherein a material of the protective liner comprises a non-woven, fluid repellent material, and a radiation device attached to the material.

In another embodiment of the present invention, a protective liner is provided comprising: a first material forming a collar comprising: a main collar portion, a first extension emanating from the main collar portion in a first direction, a second extension emanating from the main collar portion in a second direction opposite to the first direction, a first tie extension extending from the first extension, a second tie extension extending from the second extension, a chest portion extending from the main collar portion, wherein a material of the protective liner comprises a non-woven material, a second material coating a surface of the first material, wherein the second material is fluid repellent, and a radiation device attached to the first material.

In still another embodiment of the present invention, a protective liner is provided comprising: a main collar portion, a first extension emanating from the main collar portion in a first direction, a second extension emanating from the main collar portion in a second direction opposite to the first direction, a chest portion extending from the main collar portion, and an adjustable releasable fastener for joining the first extension to the second extension, the adjustable releasable fastener disposed upon at least one of the first extension and second extension, wherein a material of the protective liner comprises a non-woven, fluid repellent material, wherein the material of the protective liner is configured to be folded upon itself for storage or packaging.

In another embodiment of the present invention, a protective liner is provided comprising: a first material forming a collar comprising: a main collar portion, a first extension emanating from the main collar portion in a first direction, a second extension emanating from the main collar portion in a second direction opposite to the first direction, a chest portion extending from the main collar portion, an adjustable releasable fastener for joining the first extension to the second extension, the adjustable releasable fastener disposed upon at least one of the first extension and second extension, wherein a material of the protective liner comprises a non-woven material, and a second material coating a surface of the first material, wherein the second material is fluid repellent, wherein the first material and the second material of the protective liner are configured to be folded upon itself for storage or packaging.

In still another embodiment of the present invention, a protective liner is provided comprising: a collar comprising: a main collar portion, a first extension emanating from the main collar portion in a first direction, a second extension emanating from the main collar portion in a second direction opposite to the first direction, a first tie extension extending from the first extension, a second tie extension extending from the second extension, and a chest portion extending from the main collar portion, wherein a material of the protective liner comprises a non-woven, fluid repellent material, wherein the material of the protective liner is configured to be folded upon itself for storage or packaging.

In another embodiment of the present invention, a protective liner is provided comprising: a first material forming a collar comprising: a main collar portion, a first extension emanating from the main collar portion in a first direction, a second extension emanating from the main collar portion in a second direction opposite to the first direction, a chest portion extending from the main collar portion, an adjustable releasable fastener for joining the first extension to the second extension, the adjustable releasable fastener disposed upon at least one of the first extension and second extension, wherein a material of the protective liner comprises a non-woven material, and a second material coating a surface of the first material, wherein the second material is fluid repellent, wherein the first material and the second material of the protective liner are configured to be folded upon itself for storage or packaging.

There has thus been outlined, rather broadly, certain embodiments of the invention in order that the detailed description of the invention herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and being practiced and carried out in various ways. Also, it is to be understood that the phraseology and terminology employed herein, as well as in the abstract, are for the purpose of description and should not be regarded as limiting.

As such, those skilled in the art will appreciate that the concept upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The accompanying drawings, which are incorporated herein and constitute part of this specification, illustrate exemplary embodiments of the invention and, together with the detailed description given below, serve to explain the features of the invention.

FIG. 2 illustrates a frontal view of the protective liner of FIG. 1 in accordance with an embodiment of the invention;

FIGS. 7A-7C illustrate views of a protective liner having a fastening means in accordance with a third embodiment of the invention;

DETAILED DESCRIPTION OF THE PREFERRED EMBODIMENTS

Definitions

Figure 1:
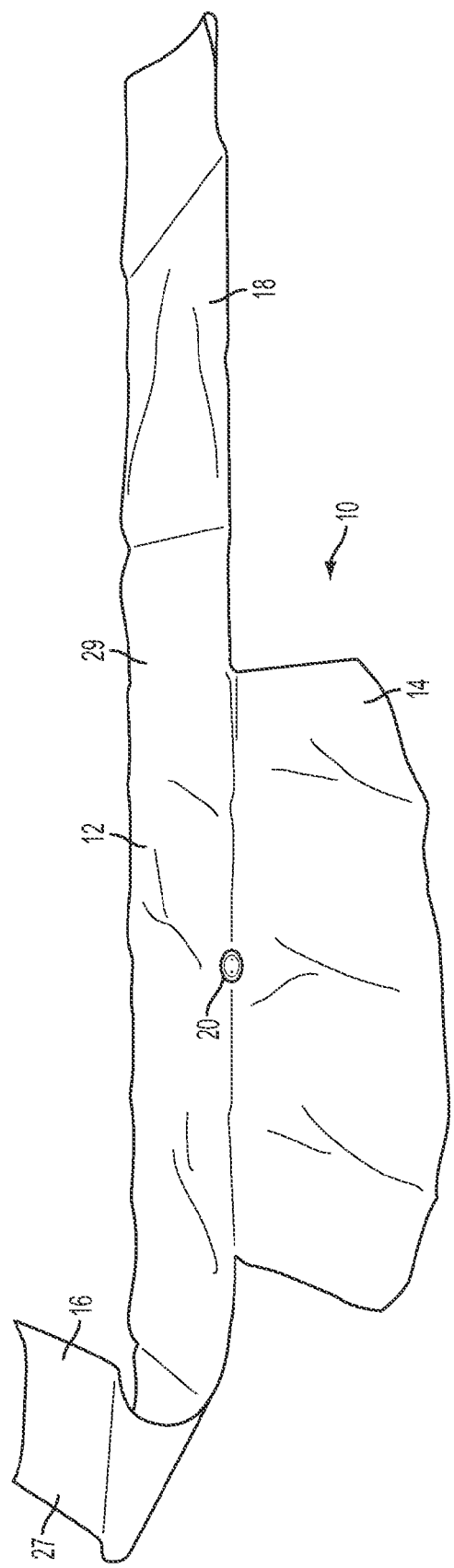
FIG. 1 illustrates a protective liner in accordance with an embodiment of the invention.

Where the definition of a term departs from the commonly used meaning of the term, applicant intends to utilize the definitions provided below, unless specifically indicated.

A "bib" is used to describe a garment worn hanging from the neck and extending to the chest area of a person.

"Electromagnetic radiation" (EM radiation or EMR) is meant to refer to a form of energy emitted and absorbed by charged particles, which exhibits wave-like behavior as it travels through space. EMR has both electric and magnetic field components, which oscillate in phase perpendicular to each other and perpendicular to the direction of energy and wave propagation. In vacuum, electromagnetic radiation propagates at a characteristic speed, the speed of light. EMR carries energy—sometimes called radiant energy—and both momentum and angular momentum. These may be imparted to matter with which it interacts. EMR is produced from other types of energy when created, and it is converted to other types of energy when it is destroyed. The photon is the quantum of the electromagnetic interaction, and is the basic "unit" or constituent of all forms of EMR. The quantum nature of light becomes more apparent at high frequencies (or high photon energy). Such photons behave more like particles than lower-frequency photons do. In classical physics, EMR is considered to be produced when charged particles are accelerated by forces acting on them. Electrons are responsible for emission of most EMR because they have low mass, and therefore are easily accelerated by a variety of mechanisms. Rapidly moving electrons are most sharply accelerated when they encounter a region of force, so they are responsible for producing much of the highest frequency electromagnetic radiation observed in nature. Quantum processes can also produce EMR, such as when atomic nuclei undergo gamma decay, and processes such as neutral pion decay. EMR is classified according to the frequency of its wave. The electromagnetic spectrum, in order of increasing frequency and decreasing wavelength, consists of radio waves, microwaves, infrared radiation, visible light, ultraviolet radiation, X-rays and gamma rays. The eyes of various organisms sense a small and somewhat variable window of frequencies of EMR called the visible spectrum. The effects of EMR upon biological systems (and also to many other chemical systems, under standard conditions) depends both upon the radiation's power and frequency. For lower frequencies of EMR up to those of visible light (i.e., radio, microwave, infrared), the damage done to cells and also to many ordinary materials under such conditions is determined mainly by heating effects, and thus by the radiation power. By contrast, for higher frequency radiations at ultraviolet frequencies and above (i.e., X-rays and gamma rays) the damage to chemical materials and living cells by EMR is far larger than that done by simple heating, due to the ability of single photons in such high frequency EMR to damage individual molecules chemically.

"Mammogram" is meant to refer to the technique of using X-rays to examine the breast in the early detection of cancer.

"Oncology" is meant to refer to the branch of medical science dealing with tumors, including the origin, development, diagnosis, and treatment of malignant neoplasms.

A "radiation shield" is used to describe a lead shield that can be put over a patient to prevent radiation from spreading to parts other than the part of the body being tested during a radiological process.

"Radiology" is meant to refer to the science dealing with X-rays and the interpretation of medical X-ray photographs especially for medical uses. Radiology is a medical specialty that employs the use of imaging to both diagnose and treat disease visualized within the human body. Radiologists use an array of imaging technologies (such as X-ray radiography, ultrasound, computed tomography (CT), nuclear medicine, positron emission tomography (PET) and magnetic resonance imaging (MRI)) to diagnose or treat diseases.

"Radiological" is of, relating to, or concerning radiology or the equipment used in radiology.

"Radiograph" is meant to refer to an image produced on a radio-sensitive surface, such as photographic film, by radiation other than visible light, as by X-rays passed through an object.

"Non-woven fabric" is meant to refer to fabric-like material made from long fibers, bonded together by chemical, mechanical, heat or solvent treatment. Nonwoven fabrics are broadly defined as sheet or web structures bonded together by entangling fiber or filaments (and by perforating films) mechanically, thermally or chemically. They may comprise flat sheets that are made directly from separate fibers or from molten plastic or plastic film. They are not made by weaving or knitting and do not require converting the fibers to yarn. Typically, a certain percentage of recycled fabrics and oil-based materials are used in non-woven fabrics. Non-woven fabrics are engineered fabrics that may be a limited life fabric, single-use fabric or a very durable fabric. Non-woven fabrics provide specific functions such as absorbency, liquid repellence, resilience, stretch, softness, strength, flame retardancy, washability, cushioning, filtering, use as a bacterial barrier and sterility. These properties are often combined to create fabrics suited for specific jobs, while achieving a good balance between product use/life and cost.

"Radiation dosimeter" is meant to refer to a device for measuring exposure to ionizing radiation such as X-rays, alpha rays, beta rays, and gamma rays.

"Radiolucent" is meant to refer to anything that permits the penetration and passage of X-rays or other forms of radiation.

"Spun-melt-spun" (SMS) is meant to refer to certain types of non-woven fabric, because they comprise superimposing spun layers on melted layers on more spun layers.

"Thyroid" is meant to refer to one of the largest endocrine glands. The thyroid gland is found in the neck, below (inferior to) the thyroid cartilage (which forms the laryngeal prominence, or "Adam's apple"). The isthmus (the bridge between the two lobes of the thyroid) is located inferior to the cricoid cartilage.

"X-ray," X-radiation (composed of X-rays) is meant to refer to a form of electromagnetic radiation. X-rays have a wavelength in the range of 0.01 to 10 nanometers (nm), corresponding to frequencies in the range 30 petahertz to 30 exahertz ($3 \times 10^{16}$ Hz to $3 \times 10^{19}$ Hz) and energies in the range 120 eV to 120 keV. They are shorter in wavelength than UV rays and longer than gamma rays. X-rays from about 0.12 to 12 keV (10 to 0.10 nm wavelength) are classified as "soft" X-rays, and from about 12 to 120 keV (0.10 to 0.01 nm wavelength) as "hard" X-rays, due to their penetrating abilities. Hard X-rays can penetrate solid objects, and their most common use is to take images of the inside of objects in diagnostic radiography and crystallography. As a result, the term X-ray is metonymically used to refer to a radiographic image produced using this method, in addition to the method itself. By contrast, soft X-rays hardly penetrate matter at all; the attenuation length of 600 eV (~2 nm) X-rays in water is less than 1 micrometer. Thus, X-rays, a form of electromagnetic radiation, similar to light but of shorter wavelength are capable of penetrating solids and of ionizing gases to produce a picture produced by exposing photographic film to X-rays. X-rays may be used in medicine as a diagnostic aid as parts of the body, such as bones, absorb X-rays and so appear as opaque areas on the photographic film.

Description

The invention will now be described with reference to the drawing figures, in which like reference numerals refer to like parts throughout. The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Turning to FIGS. 1 and 2, a protective liner 10 is illustrated as a disposable bib designed to keep a radiation shield (e.g., a thyroid shield) clean from patient sweat and fluids during radiological procedures such as when receiving mammograms and dental X-rays. Protective liner 10 may be utilized, for example, by mammography technicians and dental hygienists/technicians to eliminate the need for cleaning and decontamination of thyroid shields between patient usage. In the disclosed embodiment, protective liner 10 serves as a barrier between the neck and chest area of a patient and the radiation shield.

A collar is provided generally at a top region of protective liner 10. The collar is designed as a wide-strip collar portion that fits around the neck of a patient and may be secured at the back of the neck. FIGS. 1 and 2 illustrate a main collar portion, which may be generally positioned at the front of the neck. A right extension or arm 16 and left extension or arm 18 emanates from main collar portion 12. Thus, disclosed embodiments of the collar include main collar portion 12, right extension 16 and left extension 18. The, collar is designed to cover the entire neck region and may run generally along or come into contact with the chin and lower jaw area of a patient when worn. Chest portion 14 extends downwardly from and substantially perpendicular to collar portion 12 to cover the chest portion of a patient when worn. Hence, in disclosed configurations, right extension 16 and left extension 18 emanate and extend from opposite directions of main collar portion 12. As shown in FIGS. 1 and 2, right extension 16 and left extension 18 extend past a distance of the width of chest portion 14, thereby forming an overall "T" configuration of protective liner 10.

Protective liner 10 may be secured to a patient via a right extension 16 and a left extension 18. The interior surface 27 of protective liner 10 faces the patient, when worn, to directly contact the body of the patient along the neck and chest region. The exterior surface 29 of protective liner 10 faces outwardly from the patient, when worn, and is in direct contact with a radiation shield, as described below. Right extension 16 and left extension 18 are wrapped around the neck and secured together in order to fit and secure protective liner 10 to a patient.

Figure 3A:
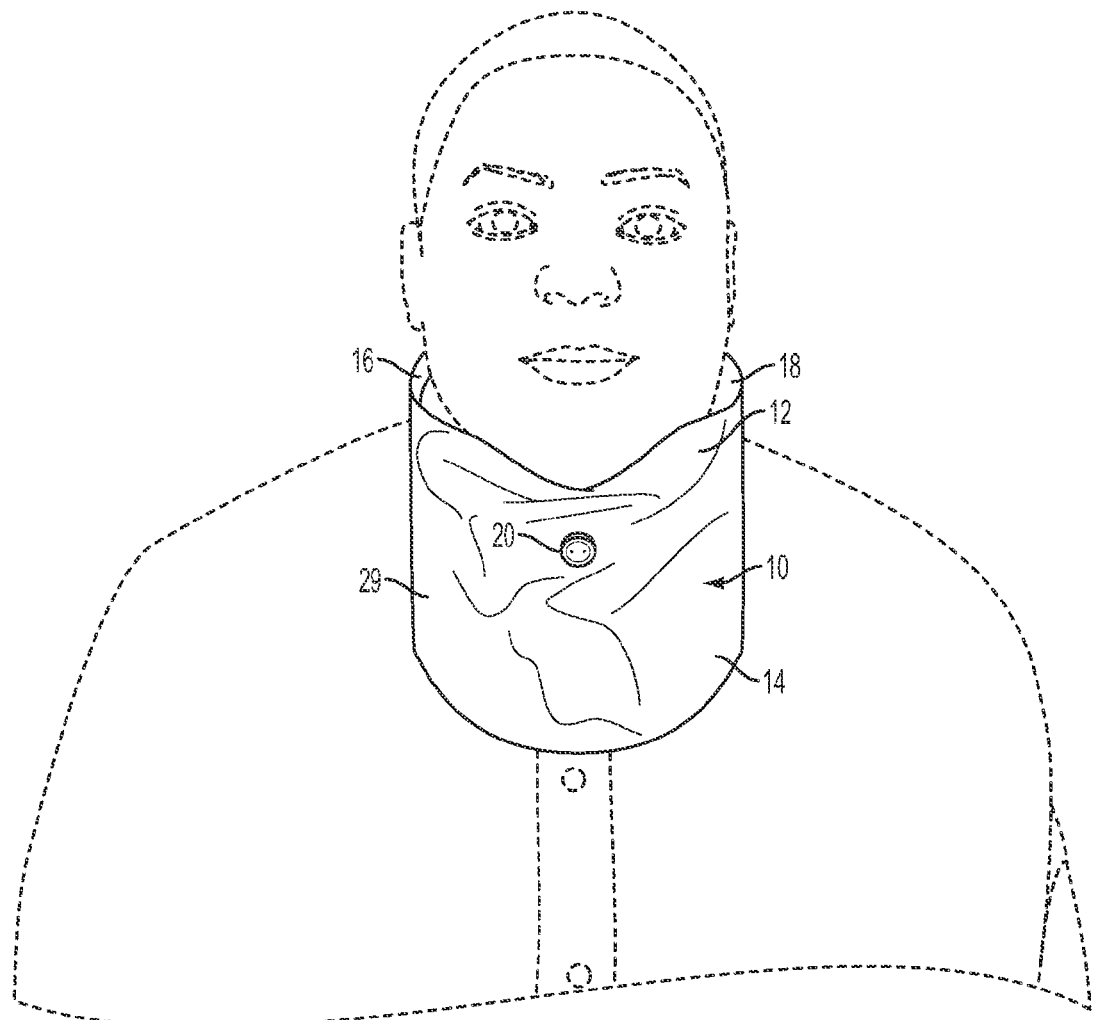
FIG. 3A illustrates a front view of the protective liner of FIG. 1 worn by a patient in accordance with an embodiment of the invention.
Figure 3B:
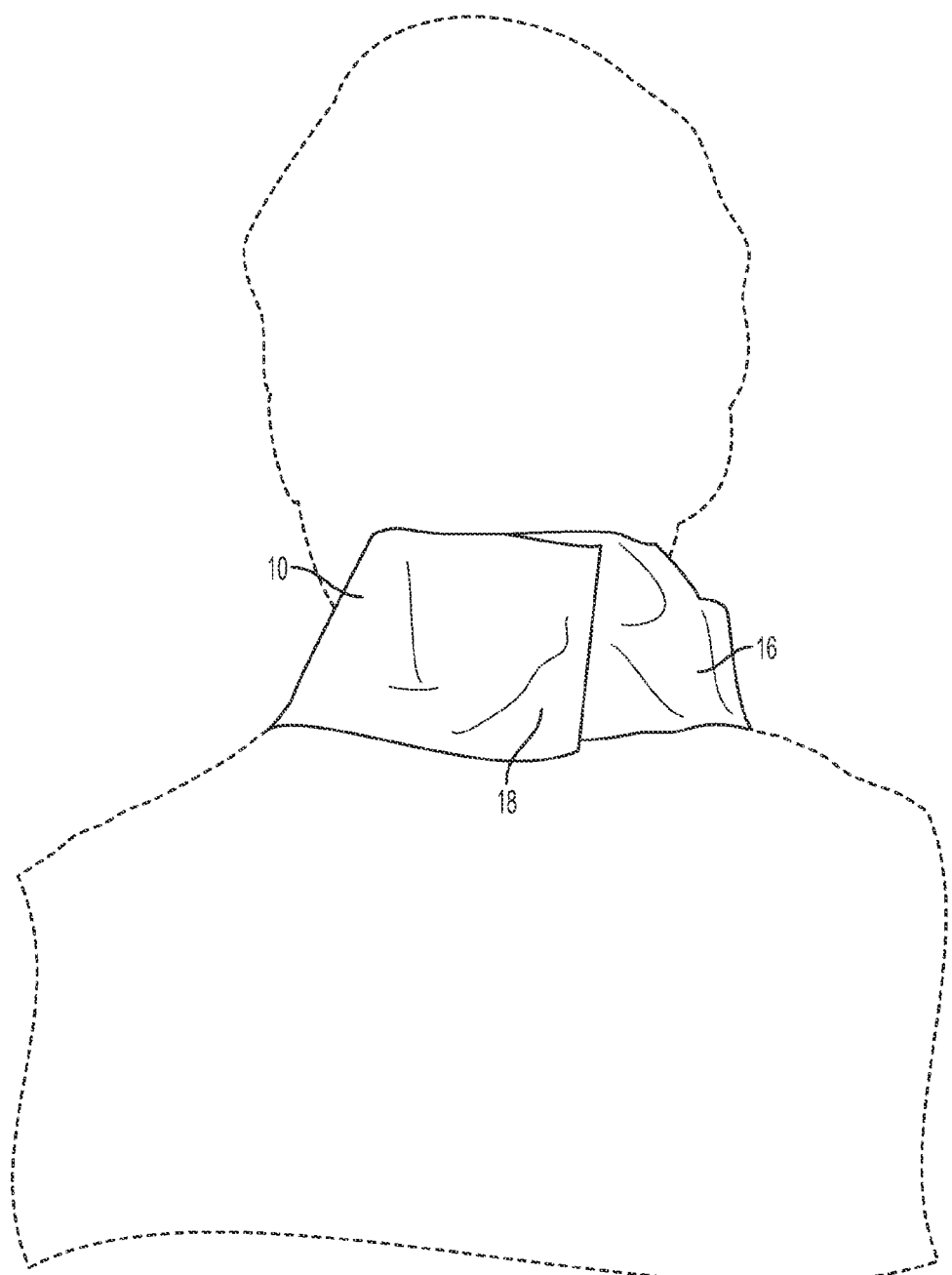
FIG. 3B illustrates a rear view of the protective liner of FIG. 1 worn by a patient in accordance with an embodiment of the invention.

As shown, for example, in FIG. 3A, once right extension 16 and left extension 18 are wrapped around the neck of a patient and secured together, the collar (comprising main collar portion 12, right extension 16 and left extension 18) is positioned substantially high around the circumference of the neck region and may even extend to generally run along or come into contact with the chin and lower jaw area of a when worn. Chest portion 14 is disposed generally downwardly and along the front chest region of the patient. FIG. 3B illustrates a rear view of protective liner 10 wherein right extension 16 and left extension 18 are fastened together behind the neck of a patient to secure protective liner 10 in position. Embodiments for a variety of fastening means for securing protective line 10 are described below. Protective liner 10 provides an overlapping of right extension 16 and left extension 18 such that no portion of the rear neck area is exposed after protective liner 10 is wrapped around the neck and secured. Disclosed embodiments of protective liner 10 also may provide adjustability of right extension 16 and/or left extension 18 to accommodate a variety of sizes to fit an assortment of patient body types. Even more, embodiments of protective liner 10 may include dimensional sizes corresponding to cover a full range of patient sizes and thyroid shields. For example, the aforementioned multiple sizes may include child, small, medium large, extra-large. Once positioned and in a secured manner, protective liner 10 is configured to conform to the shape of the body of the patient and lying generally flat against the body of the patient such that relatively no bunching is permitted to, thereby, allow exposure of a covered body portion and/or clothing material of the patient.

Figure 4A:
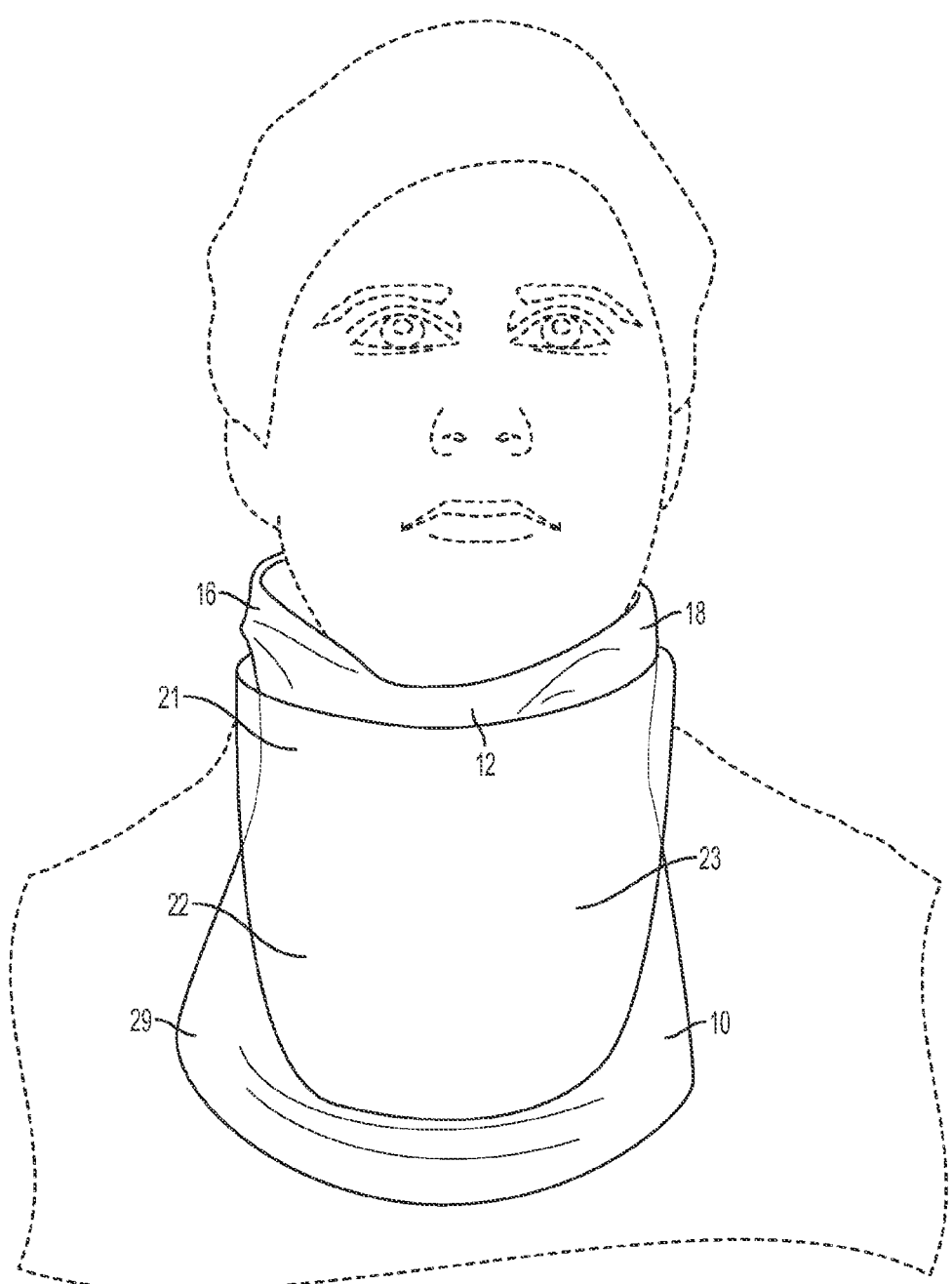
FIG. 4A illustrates a front view of the protective liner of FIG. 1 employed underneath a radiation shield worn by a patient in accordance with an embodiment of the invention.
Figure 4B:
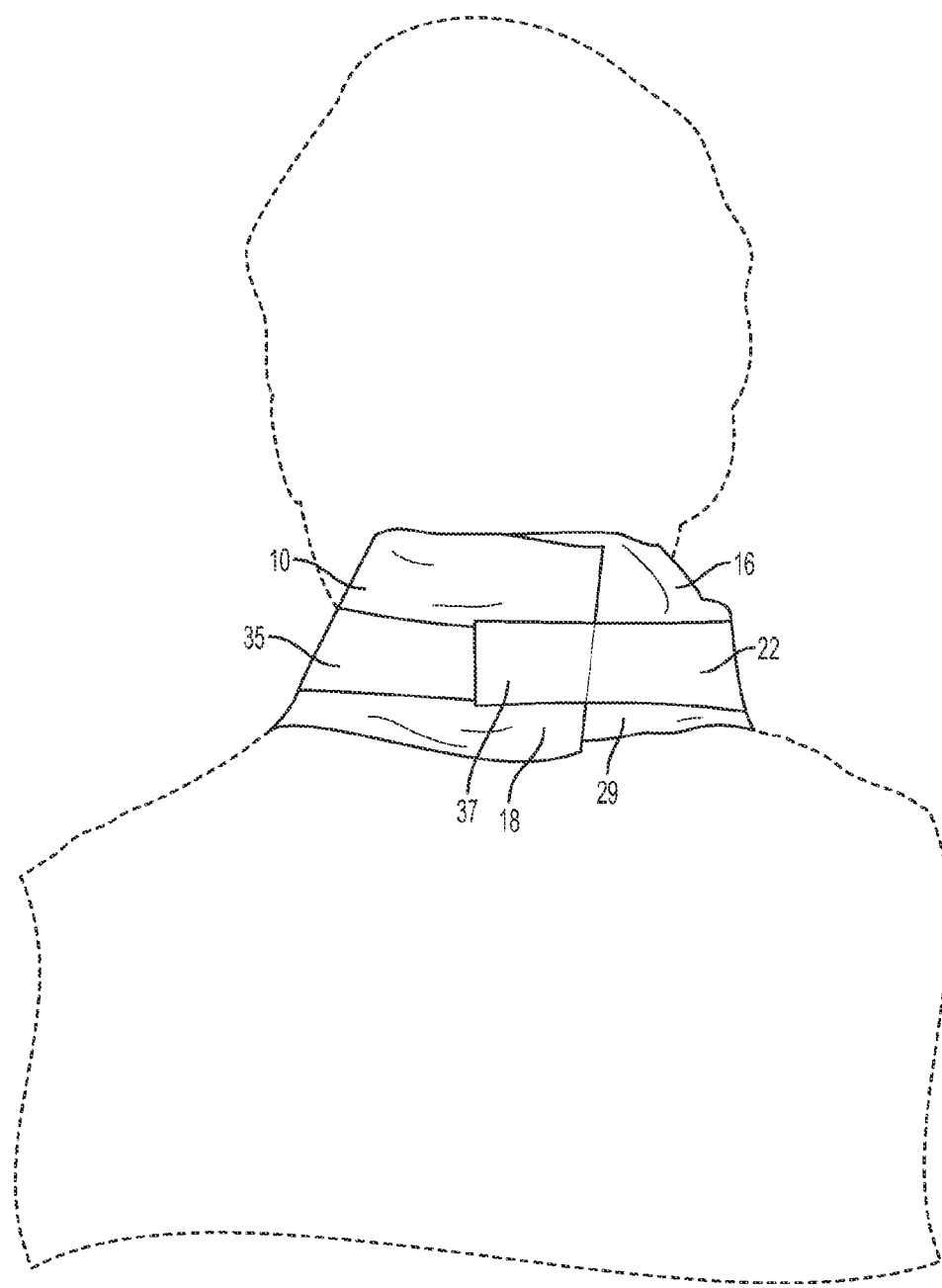
FIG. 4B illustrates a rear view of the protective liner of FIG. 1 employed underneath a radiation shield worn by a patient in accordance with an embodiment of the invention.

Turning to FIG. 4A, a radiation shield 22 is fitted and secured over protective liner 10 and around the neck of a patient. In the disclosed embodiment, radiation shield 22 is utilized as a thyroid shield employed to protect the thyroid region against exposure to radiation during a radiological process. Radiation shield 22 may generally be designed to include a collar portion 21 which generally fits the patient at the thyroid region. A portion 23 of radiation shield 22 may extend downwardly towards the chest region. Extended arm portions 35, 37 of radiation shield 22 may wrap around the neck of a patient and connected together to secure radiation shield in position (e.g., see FIG. 4B).

During use, radiation shield 22 is positioned over and on top of exterior surface 29 of protective liner 10. Disclosed embodiments of protective liner 10 are designed to be larger and lie under radiation shield 22 wherein protective liner 10 is affixed by joining right extension 16 to left extension 18 behind the neck of a patient. Hence, the dimensions of protective liner 10 are generally larger than the dimensions of radiation shield 22 in order to prevent radiation shield 22 from coming into direct contact with the patient and/or clothing worn by the patient. Accordingly, portions of radiation shield 22, for example, resting upon the chest and around the neck of the patient are shielded from direct contact with the patient by protective liner 10. By aligning protective liner 10 under radiation shield 22 in the disclosed manner, no transfer of sweat and/or other fluids from the patient may occur to radiation shield 22. In effect, protective liner 10 acts as a barrier between the neck and chest of a patient and radiation shield 22. Once the radiological procedure is complete, radiation shield 22 is simply removed from the patient with no portion of radiation shield 22 coming into contact with the patient. Once radiation shield 22 is removed from the patient, protective liner 10 may be unsecured, removed and discarded, as discussed below.

Components of protective liner 10 including, for example, main collar portion 12, chest portion 14, right extension 16 and left extension 18 may be formed as a unitary structure, such as from a pre-selected material as described herein. Disclosed material utilized for protective liner 10 may include a soft, hypoallergenic, non-woven, latex-free, material. The material is pliable to achieve the shape of a body portion or region while remaining relative flat against a body contour thereof Select embodiments may include protective liner 10 as a fabric material that is fluid repellent to prevent sweat or other bodily fluid from penetrating the material. Accordingly, the aforementioned fabric material may include non-woven fabric of an SMS (spun-melt-spun) plastic material, for example, having a prescribed tensile strength. A coating may be applied to surfaces of the SMS material such as a polypropylene and polyethylene laminate to facilitate fluid repellency of the material. Protective liner 10 may be supplied in a variety of colors including, for example, medical blue, green, white, purple or orange. In addition, embodiments of the material of protective liner 10 may be printable, for example, to exhibit a logo or office design. The material of protective liner 10 is also radiolucent, disposable and tear free.

Select embodiments of the present invention may incorporate additional equipment or devices to the design of protective liner 10. For example, turning to FIGS. 1-3A, a radiation device, such as dosimeter 20 is provided, for example, on the exterior surface 29 of protective liner 10. Any suitable connection means may be utilized to attach dosimeter 20, for example, to the exterior surface 29 of protective liner 10. Thus, dosimeter 20 may be retrofitted within the material of protective liner 10. Dosimeter 20 is generally disposed along a region of protective liner corresponding to a position over a prescribed body part being tested during a radiological process. In this case, dosimeter 20 is generally disposed at an area corresponding to a position over the thyroid region. When radiation shield 22 is positioned over protective liner 10, dosimeter 20 will indicate (e.g., via change of color) whether any measured amounts of ionizing radiation have penetrated this area during a radiological procedure. Additional and/or alternative devices may be utilized as or in place of dosimeter 20 including, for example, Inlight® nanoDot™ utilized for diagnostic radiology, therapy, or any single point radiation assessment application.

Figure 5B:
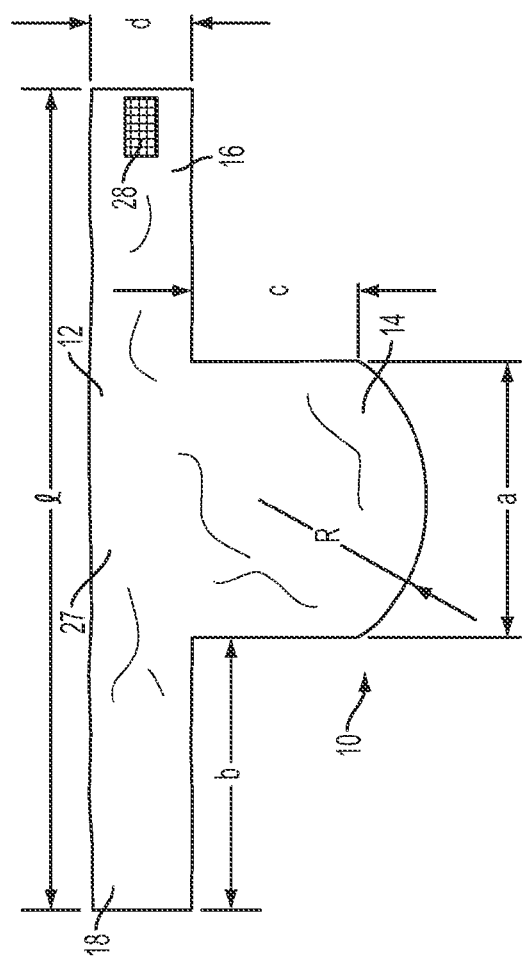
FIGS. 5A-5C illustrate views of a protective liner having a fastening means in accordance with a first embodiment of the invention.
Figure 5A:
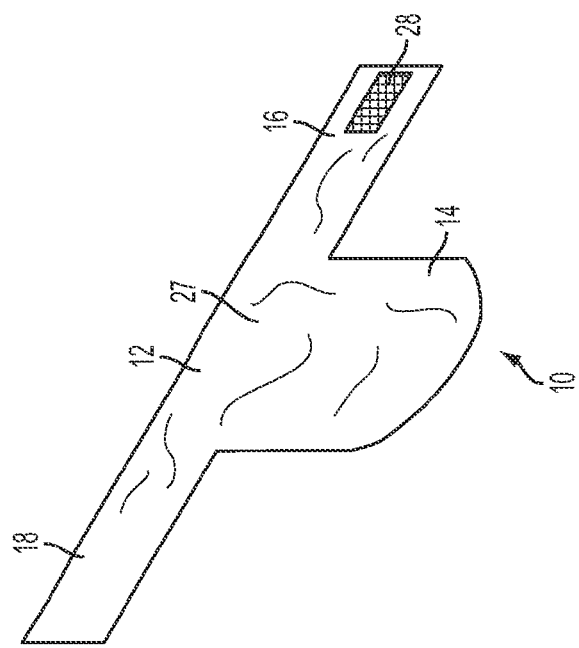
Figure 5C:
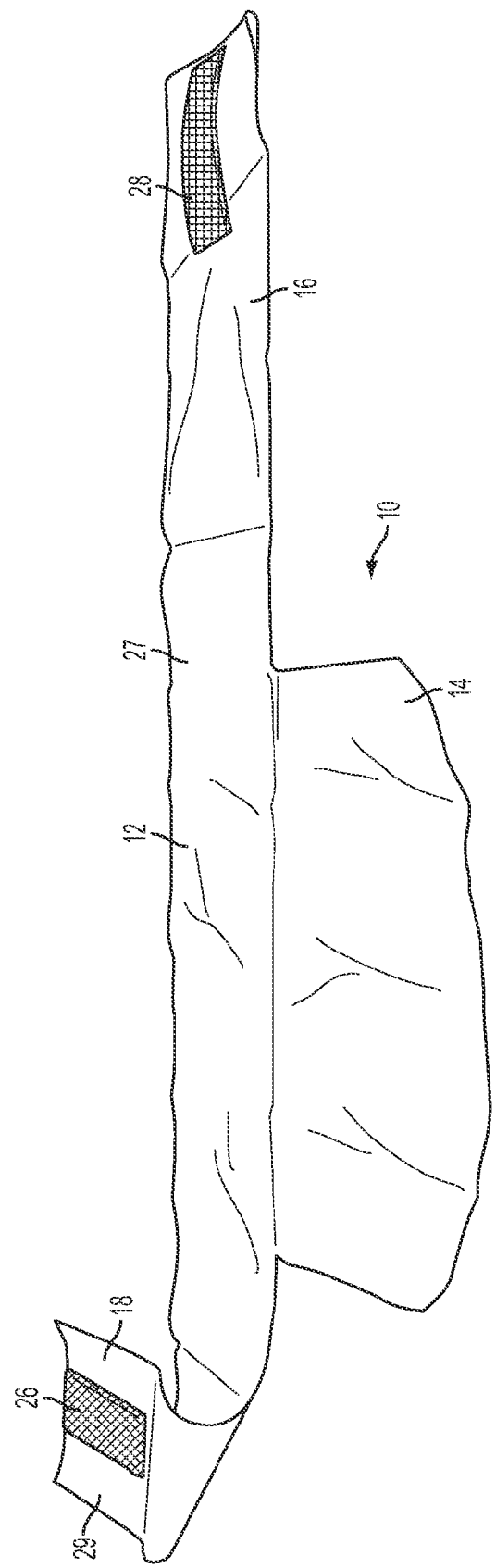

FIGS. 5A-5C illustrate a first embodiment of protective liner 10 having a releasable fastener wherein one end of the collar has a fastening means with a weaker fastening strength than the other end of the collar. Exemplary embodiments of the invention may includes a loop element 26 and hook element 28 of a hook and loop fastener, i.e., a VELCRO® fastener. In the disclosed embodiment, hook element 28 is attached to the interior surface 27 of right extension 16 and loop element 26 is attached to the exterior surface 29 of left extension 18 by any suitable attachment means. When right extension 16 and left extension 18 are wrapped around the neck of a patient, loop element 26 and hook element 28 are engaged to couple loop elements 26 together with hook elements 28 in order to secure protective liner 10 around the neck. It is expected that right extension 16 may overlap left extension 18 during fastening so that no portion of the neck area is exposed. Both portions of the loop element 26 and hook element 28 are sufficiently provided in order to adjust right extension 16 and left extension 18 with respect to one another to allow the collar to accommodate a variety of bodily dimensions of the patient. When secured in the aforementioned manner, interior surface 27 of collar portion 12 rests substantially flat against the neck area of the patient. Additionally, interior surface 27 of chest portion 14 lies relatively flat against the chest of the patient.

Figure 6B:
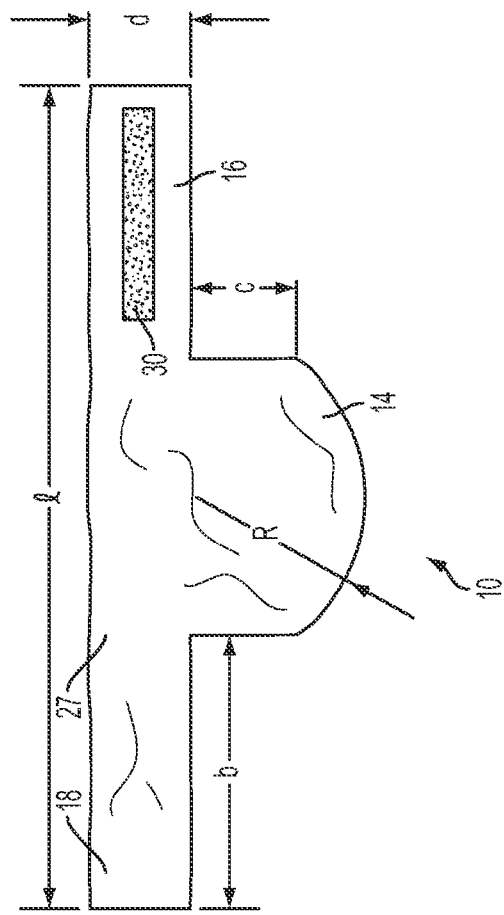
FIGS. 6A-6C illustrate views of a protective liner having a fastening means in accordance with a second embodiment of the invention.
Figure 6A:
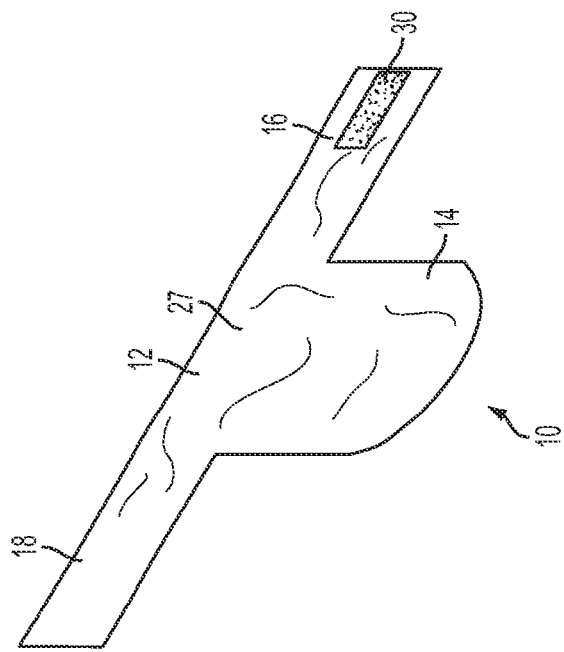
Figure 6C:
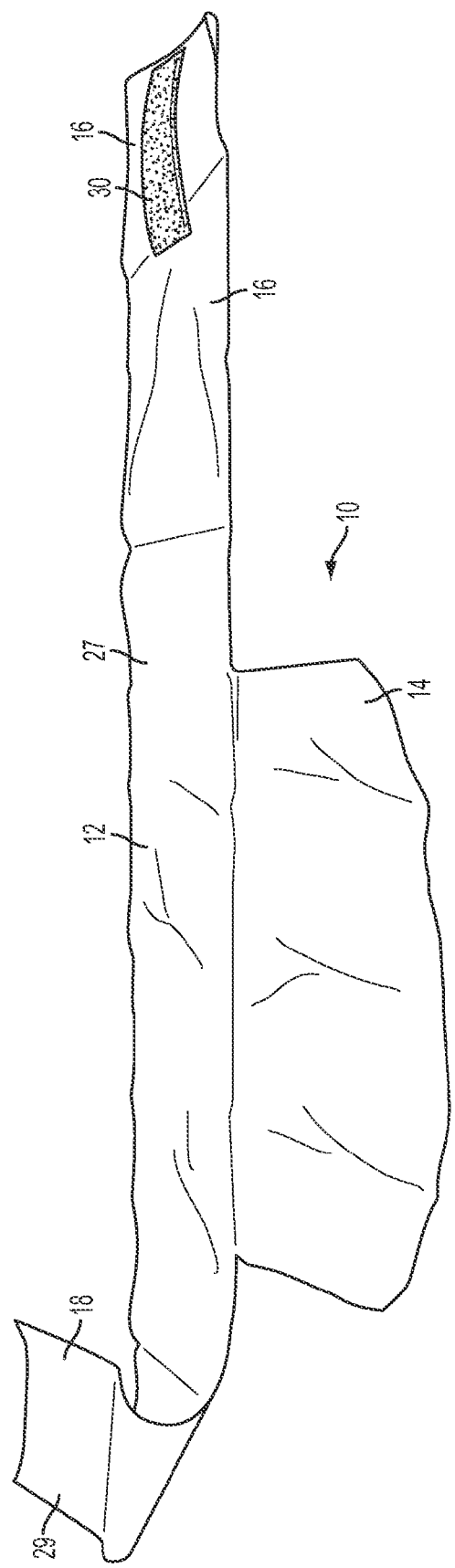

FIGS. 6A-6C illustrate a second embodiment of protective liner 10 having a releasable fastener such as an adhesive element 30. In select embodiments, adhesive element 30 may comprise double-sided tape. One side of adhesive element 30 may be attached to the interior surface 27 of right extension 16. The exposed side of adhesive element 30 may be utilized to join exterior surface 29 of left extension 18. In the exemplary embodiment wherein adhesive element 30 comprises double-sided tape, the exposed side of the double-sided tape may be covered with a removable cover until protective liner 10 is ready for use. When protective liner 10 is ready for use, the removable cover is removed from the exposed side of the double-sided tape. When right extension 16 and left extension 18 are wrapped around the neck of a patient, the exposed side of the double-sided tape (i.e., adhesive element 30) may be affixed to exterior surface 29 of left extension 18 in order to secure protective liner 10 around the neck. It is expected that right extension 16 may overlap left extension 18 during fastening so that no portion of the neck area is exposed. Portions of adhesive element 30 are sufficiently provided in order to adjust right extension 16 and left extension 18 with respect to one another to allow the collar to accommodate a variety of bodily dimensions of the patient. When secured in the aforementioned manner, interior surface 27 of the collar rests substantially flat against the neck area of the patient. Additionally, interior surface 27 of chest portion 14 lies relatively flat against the chest of the patient.

FIGS. 7A-7C illustrate a third embodiment of protective liner 10 having a releasable fastener such as a slip-through-and-catch design. In the disclosed embodiment, the slip-through-and-catch design includes etched fastener portions 32 configured into the design of right extension 16. Outside edges 19 of right extension 16 taper towards the middle 44 to form reduced portions 41. Reduced portions 41 may taper back to increased portions 39 at outside edges 19. A series of reduced and increased portions may be formed from the surface of right extension 16 to create etched fastener portions 32. Therefore, a design of the etched fastener portions 32 forms reduced portions 41 between increased portions 39. In exemplary embodiments, the material of protective liner 10 may be stamped out to form etched fastener portions 32. Once formed, spaces 43 are formed between increased portions 39. Any suitable number of increased portions 39 and reduced portions 41 may be formed on right extension 16 to provide adjustability of the collar around the neck of a patient, as described below. The described embodiment provides a slot 34 to receive one or more increased portions 39 of etched fastener portions 32 therethrough to secure protective liner 10 around the neck of the patient. Slot 34 may fall into alignment with one of spaces 43 between increased portion 39, thereby fixing the collar in place around the neck of a patient. The increased portions 39 surrounding space 43 act as stops and will prevent right extension 16 from becoming unfastened from slot 34. Any appropriate space may be selected to fit the collar securely around the neck of a patient. It is expected that right extension 16 may overlap left extension 18 during fastening so that no portion of the neck area is exposed. Multiple spaces 43 are sufficiently provided in order to adjust right extension 16 and left extension 18 with respect to one another to allow the collar to accommodate a variety of bodily dimensions of the patient. The length "z" of etched portions 32 along right extension 16 may be established between a range of sizes. For example, in one select embodiment, the length "z" is 5.50 inches. When secured in the aforementioned manner, interior surface 27 of the collar rests substantially flat against the neck area of the patient. Additionally, interior surface 27 of chest portion 14 lies relatively flat against the chest of the patient.

Figure 8B:
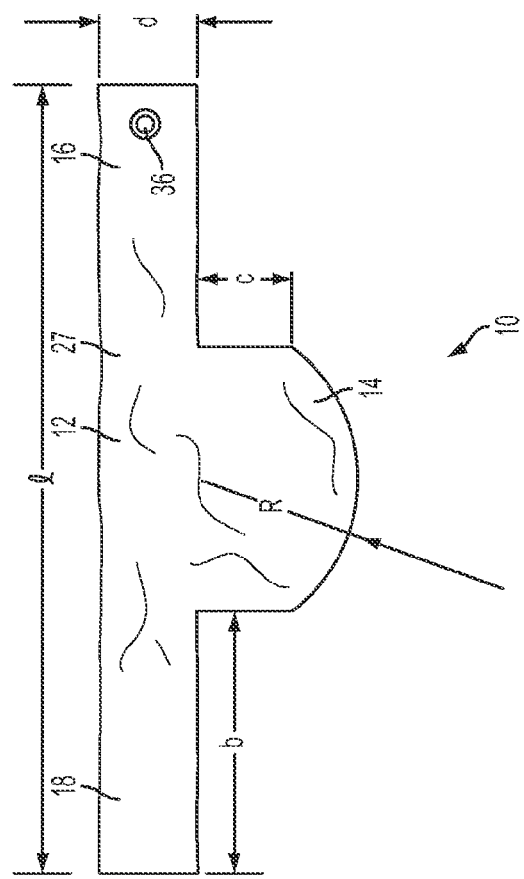
FIGS. 8A-8C illustrate views of a protective liner having a fastening means in accordance with a fourth embodiment of the invention.
Figure 8A:
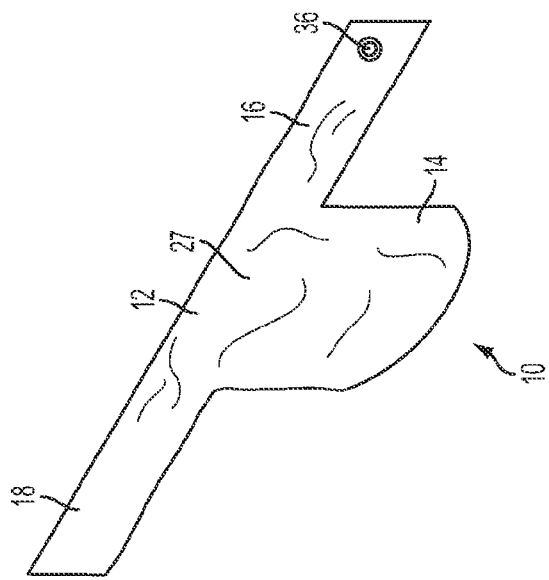
Figure 8C:
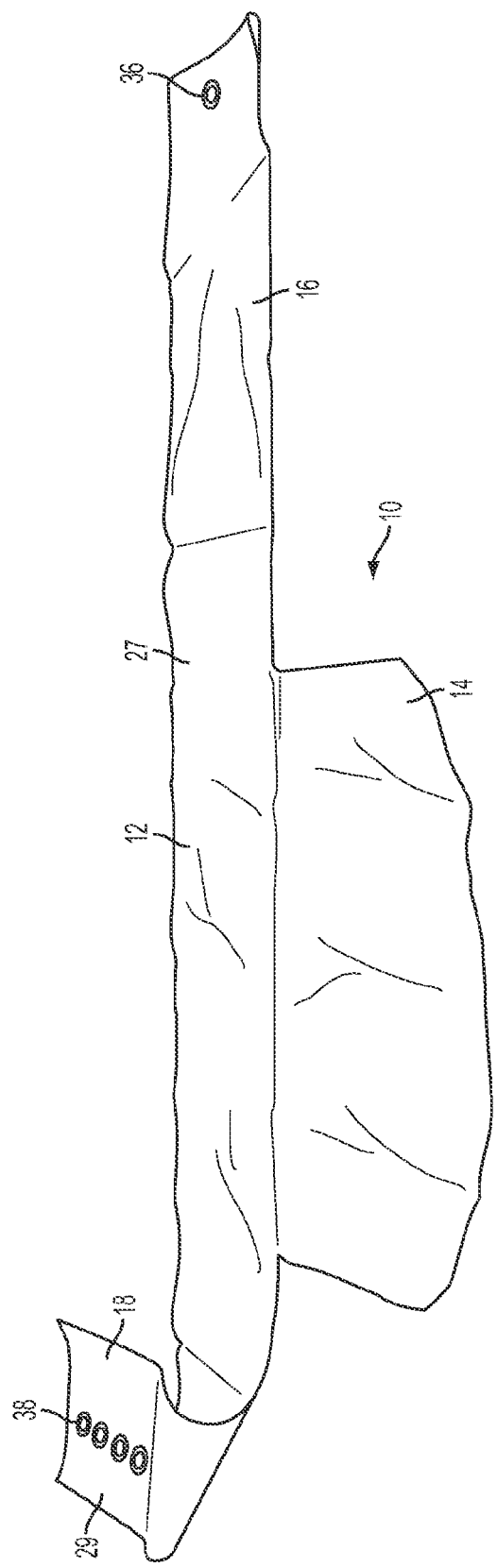

FIGS. 8A-8C illustrate a fourth embodiment of protective liner 10 having a releasable fastener such as a button and snap design. In the disclosed embodiment, a button 36 is attached to the interior surface 27 of right extension 16 by any suitable attachment means. A plurality of snaps 38 are attached to the exterior surface 29 of left extension 18 by any suitable attachment means. When right extension 16 and left extension 18 are wrapped around the neck of a patient, button 36 may engage and couple with any one of snaps 38 to secure protective liner 10 around the neck of a patient. Coupling may occur by snap-fit arrangement. It is expected that right extension 16 may overlap left extension 18 during fastening so that no portion of the neck area is exposed. Multiple snaps 38 are provided along the length of left extension 18 in order to provide selective adjustment of right extension 16 with respect to left extension 18, thereby allowing the collar to accommodate a variety of bodily dimensions of the patient. When secured in the aforementioned manner, interior surface 27 of the collar rests substantially flat against the neck area of the patient. Additionally, interior surface 27 of chest portion 14 lies relatively flat against the chest of the patient.

Figure 9B:
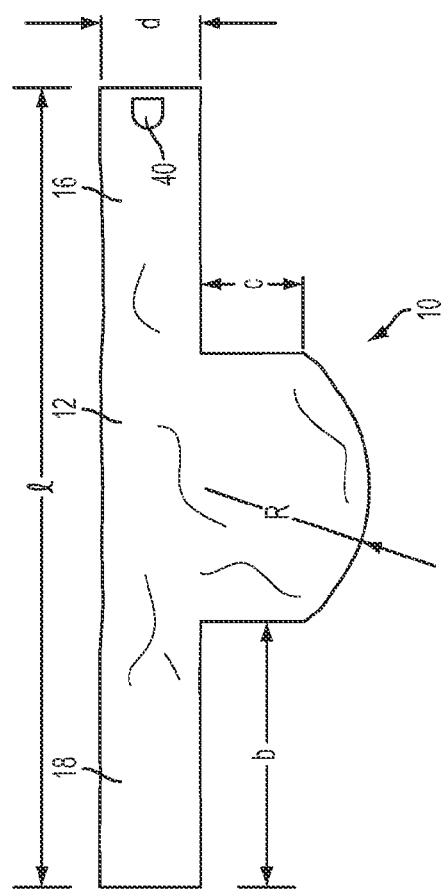
FIGS. 9A-9C illustrate views of a protective liner having a fastening means in accordance with a fifth embodiment of the invention.
Figure 9A:
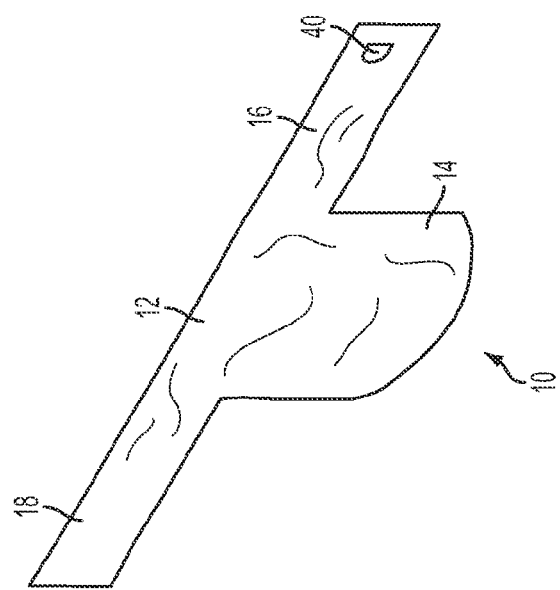
Figure 9C:
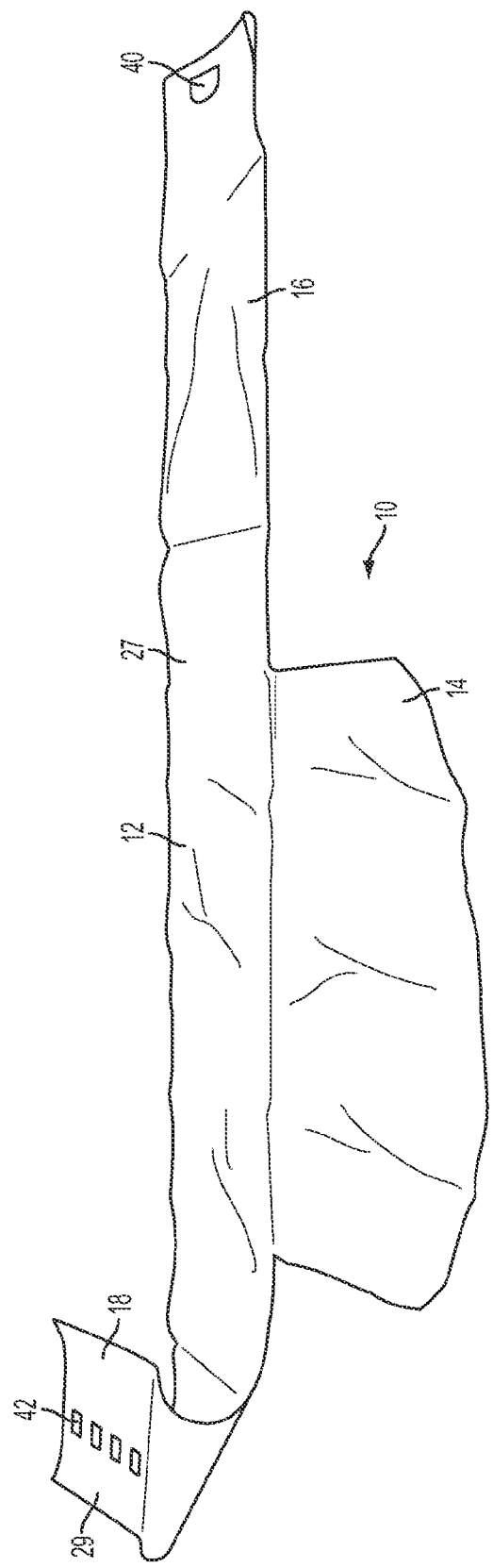

FIGS. 9A-9C illustrate a fifth embodiment of protective liner 10 having a releasable fastener such as clip fastener and tab design. In the disclosed embodiment, a clip fastener 40 is attached to the interior surface 27 of right extension 16 by any suitable attachment means. A plurality of tabs 42 are attached to the exterior surface 29 of left extension 18 by any suitable attachment means. When right extension 16 and left extension 18 are wrapped around the neck of a patient, clip fastener 40 may engage and couple with any one of tabs 42 to secure protective liner 10 around the neck of a patient. Coupling may occur by clip fastener 40 latching onto one of tabs 42. It is expected that right extension 16 may overlap left extension 18 during fastening so that no portion of the neck area is exposed. Multiple tabs 42 are provided along the length of left extension 18 in order to provide selective adjustment of right extension 16 with respect to left extension 18, thereby allowing the collar to accommodate a variety of bodily dimensions of the patient. When secured in the aforementioned manner, interior surface 27 of the collar rests substantially flat against the neck area of the patient. Additionally, interior surface 27 of chest portion 14 lies relatively flat against the chest of the patient. In an alternative embodiment, tabs 42 may be replaced with slots, wherein clip fastener 40 latches onto or hooks into the slot to fasten right extension 16 to left extension 18 at a prescribed position to secure protective liner 10 around the neck of a patient.

Figure 10:
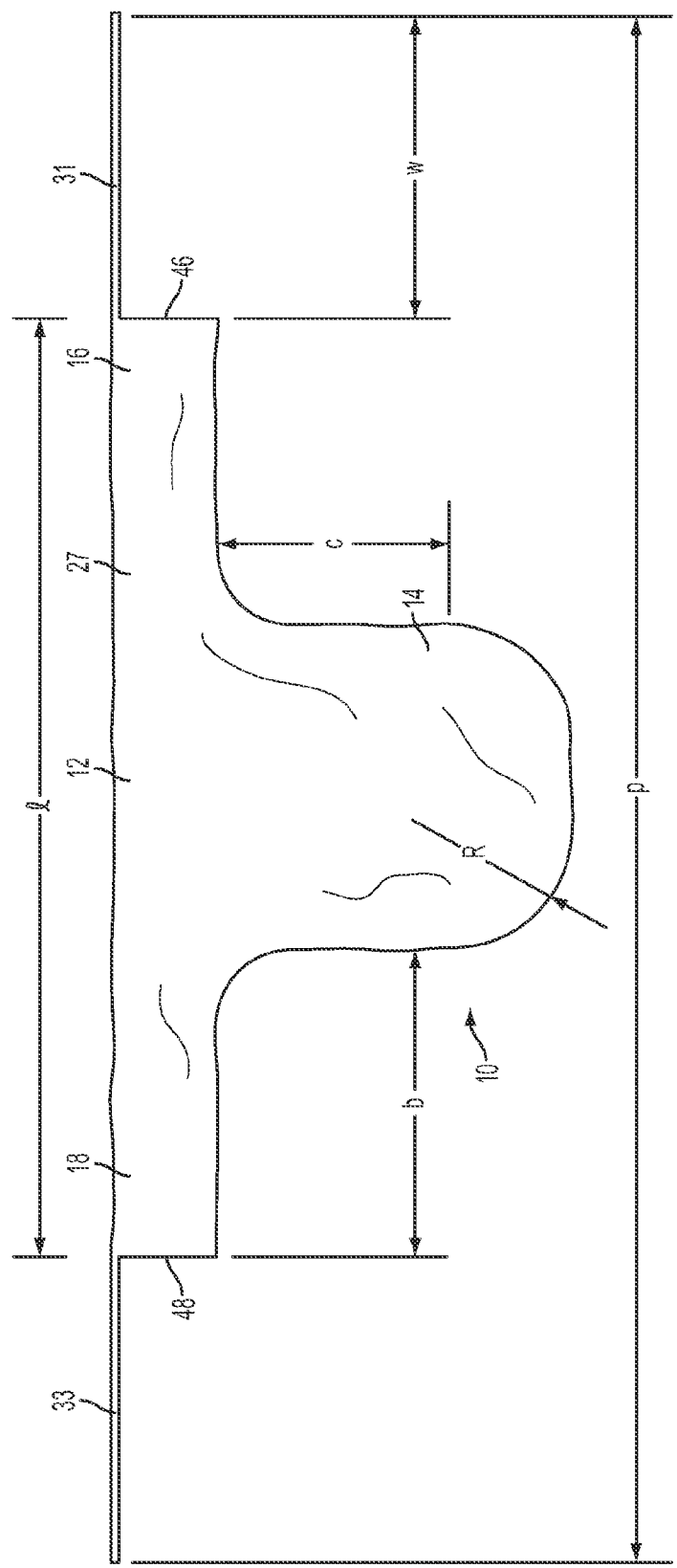
FIG. 10 illustrates a protective liner having a fastening means in accordance with a sixth embodiment of the invention.

FIG. 10 illustrates a sixth embodiment of protective liner 10 having a releasable fastener such as tie design. In the disclosed embodiment, extended pieces of material extend from the collar of protected liner 10. The extended pieces of material may form a right tie extension 31 and a left tie extension 33 as continuing pieces of material extending from right extension 16 and left extension 18, respectively. Thus, in the immediate embodiment of FIG. 10, components of protective liner 10 including, for example, main collar portion 12, chest portion 14, right extension 16, left extension 18, right tie extension 31 and left tie extension 33 may be formed as a unitary structure, such as from the pre-selected material, as described herein.

Each of the right tie extension 31 and the left tie extension 33 may comprise a width "w" established between a range of sizes. An overall or total length of the top of the collar including right tie extension 31 and left tie extension 33 may comprise a length "p" established between a range of sizes. When right extension 16 and left extension 18 are wrapped around the neck of a patient, right tie extension 31 and left tie extension 33 may be tied together to secure protective liner 10 around the neck of a patient. It is expected that right edge 46 of right extension 16 may abut or overlap the left edge 48 of left extension 18 during fastening so that no portion of the neck area is exposed. When secured in the aforementioned manner, interior surface 27 of the collar rests substantially flat against the neck area of the patient. Additionally, interior surface 27 of chest portion 14 lies relatively flat against the chest of the patient. In an alternative embodiment, tabs 42 may be replaced with slots, wherein clip fastener 40 latches onto or hooks into the slot to fasten right extension 16 to left extension 18 at a prescribed position to secure protective liner 10 around the neck of a patient.

As previously discussed, the dimensions of protective liner 10 are generally larger than the dimensions of radiation shield 22 in order to prevent radiation shield 22 from coming into direct contact with the patient and/or clothing worn by the patient. Thus, in the selected embodiments of FIGS. 5B, 6B, 7B, 8B, 9B and 10, an overall or total length "l" of the collar (i.e., main collar portion 12, right extension 16 and left extension 18) may be established between a range of sizes. The diameter formed by wrapping the length "l" of main collar portion 12, right extension 16, and left extension 18 around the neck of a patient may be adjusted by moving and positioning right extension 16 with respect to left extension 18. The embodiments of releasable fasteners, shown and described in FIGS. 5A-10, join right extension 16 and left extension 18 in a fixed position to retain protective liner 10 in place and around the neck of the patient. In some disclosed embodiments, the described releasable fasteners unite right extension 16 with left extension 18 in an overlapped fashion thereby establishing an adjusted length and diameter of the collar when wrapped around the neck of a patient. The adjusted length and diameter will meet the circumference dimensions of the neck of a patient during use. In doing so, the collar may be fit snugly around the neck of the patient and lie substantially flat against the body of the patient such that gathering or bunching of protective liner 10 material is significantly reduced or avoided.

The length "b" of each arm 16 or 18 measured from an edge of chest portion 14 to the end of arm 16 or 18 may be established between a range of sizes. A thickness "d" the collar may be established between a range of sizes. A design of chest portion 14 may include a straight portion, having a width "a," extending from main collar portion 12 and terminating at a curved end portion. The overall width "a" may be established between a range of sizes. The length "c" of the straight portion of chest portion 14 may be established between a range of sizes. The radius "R" of the curved end portion may be established between a range of sizes. Thus, in one prepared embodiment, protective liner 10 includes an overall length "l" equaling approximately 24.00 inches, wherein the thickness "d" of the collar is approximately 3.00 inches. The length of arms 16, 18 is approximately 8.00 inches. The length "c" of the straight portion of chest portion 14 is approximately 5.00 inches, wherein the width "a" of the straight portion is approximately 8.00 inches. A radius "R" of the curved portion is approximately 5.00 inches.

Figure 11A:
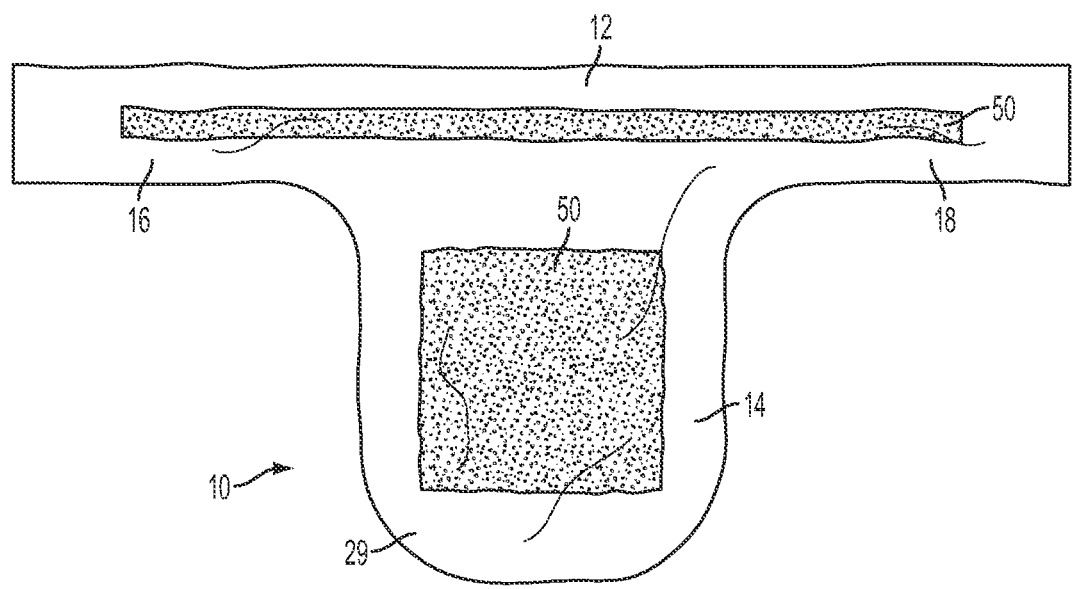
FIG. 11A illustrates a front view of a protective liner employing a retaining means to maintain a position of a radiation shield in accordance with an embodiment of the invention.

FIG. 11A illustrates an embodiment of protective liner 12 employing a retaining means to maintain a position of radiation shield 22. Select embodiments may provide securing areas 50 disposed directly on exterior surface 29 for gripping and maintaining radiation shield 22 to thereby hold radiation shield 22 in position over top of protective liner 10. While two securing areas 50 are illustrated in FIG. 11A, it is readily appreciated that more or less securing areas 50 may be provided. The dimensions of securing areas 50 may also vary in sufficiency for holding radiation shield 22 in place over top of protective liner 10. An embodiment of securing areas 50 may include covering the entire exterior surface 29, such as, with a slip-resistant material; alternatively, only select portions of exterior surface may be covered. Embodiments of securing areas 50 may include an adhesive and/or a tactile finish comprising a coefficient of friction sufficient for supporting and retaining radiation shield 22 in place over top of protective liner 10. The adhesive area may be covered until such time for usage whereupon the cover is removed to expose the adhesive for securing radiation shield 22 thereto. Such an adhesive is appropriately applied such that it is releasable by reasonable amount of force to remove radiation shield 22 therefrom. Additional embodiments may employ other finishes or retaining means including, for example, double-sided tape.

Figure 11B:
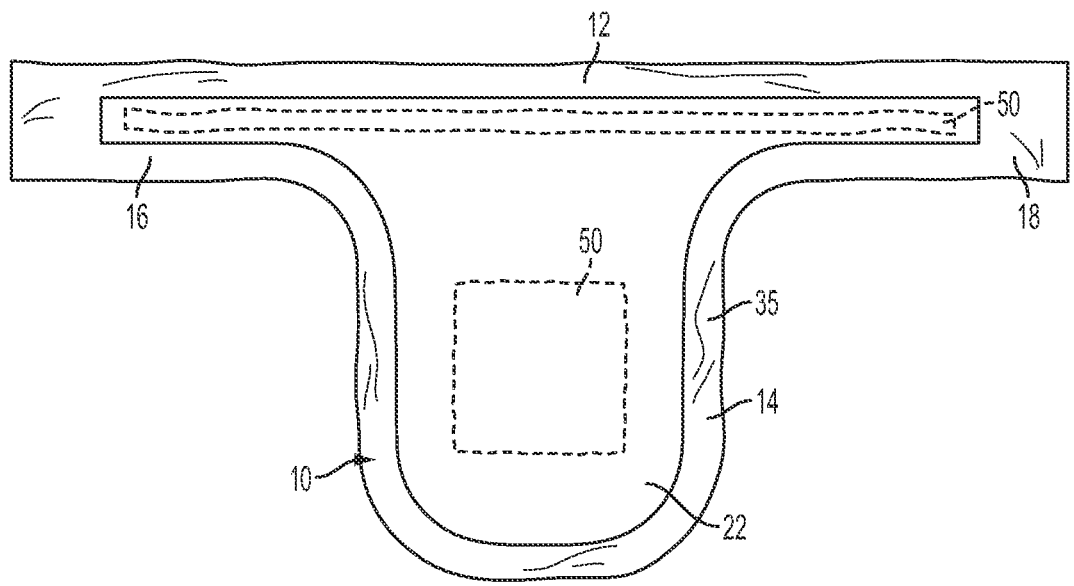
FIG. 11B illustrates the protective liner of FIG. 11A employed underneath a radiation shield in accordance with an embodiment of the invention.

Turning to FIG. 11B, radiation shield 22 is fitted over protective liner 10 and retained in position via securing areas 50. Any variety of fastening means, as described in the above embodiments, may be employed to retain protective liner 10 around the neck of the patient. Securing areas 50 facilitate retention of radiation shield 22 in position over protective liner 10 so that it does not easily move with respect to protective liner 10. When secured in the aforementioned manner, radiation shield 22 easily conforms to the shape of protective liner 10. Further, protective liner 10 protects the user from coming into contact with and possible contamination of radiation shield 22.

Disclosed embodiments of protective liner 10 may be packaged as individual liners, for example, aligned in a stacked configuration within a packaging container. The total number of protective liners 10 with the packaging container may be preselected prior to packaging. In another embodiment protective liner 10 may be stamped from a roll of material from which it is comprised (e.g., SMS fluid-repellent material) and perforated such that individual protective liners 10 may be separated from other protective liners 10 within the same roll. The stamping process may facilitate large production scale output of protective liners 10 to efficiently meet prescribed production demands. Suitable manufacturing equipment may be secured and employed to perform stamping and production operations, as necessary. Select packaging options for protective liner 10 may include shrink wrapping and/or polybagging. The material of protective liner 10 is generally foldable upon itself in any direction to facilitate storage and packaging for use. This includes any fluid repellent coating materials that may be applied to protective liner 10. There are no shelf life restrictions or claims imposed upon protective liner 10.

Thus, embodiments of the present invention provide a protective liner 10 that eliminates the need for cleaning and disinfecting radiation shields between patient use. Disclosed embodiments of protective liner 10 adequately protect the radiation shield 22 from being soiled. Protective liner 10 is applied and attached easily and comfortably to the patient. It remains attached through the radiological procedure and is easily removed from the patient after the procedure. Protective liner 10 is disposable and is sized to cover a full range of patient sizes and radiation shields. Embodiments of protective liner 10 are tear free and packaged to protect it from moisture and contamination. The material of protective liner 10 is printable, yet radiolucent. The material is also comfortable and does not make the patient feel claustrophobic. Disclosed embodiments of protective liner 10 offer no shelf life expiration. Material embodiments of protective liner 10 may include a soft, hypoallergenic, non-woven, latex-free, material.

Having described the many embodiments of the present invention in detail, it will be apparent that modifications and variations are possible without departing from the spirit and scope of the invention. Furthermore, it should be appreciated that all examples in the present disclosure, while illustrating many embodiments of the invention, are provided as non-limiting examples and are, therefore, not to be taken as limiting the various aspects so illustrated.

While the present invention has been disclosed with references to certain embodiments, numerous modifications, alterations and changes to the described embodiments are possible without departing from the spirit and scope of the present invention, as defined in the appended claims. Accordingly, it is intended that the present invention not be limited to the described embodiments, but that it have the full scope defined by the language of the following claims and equivalents thereof.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless such changes and modifications depart therefrom.

What is claimed is:

1. A protective liner comprising:
a collar comprising:
a main collar portion;
a first extension emanating from the main collar portion in a first direction;
a second extension emanating from the main collar portion in a second direction opposite to the first direction;
a chest portion extending from the main collar portion; and
an adjustable releasable fastener for joining the first extension to the second extension, the adjustable releasable fastener disposed upon at least one of the first extension and second extension, wherein a material of the protective liner comprises a non-woven, fluid repellent material.

2. The protective liner of claim 1, wherein the adjustable releasable fastener joins the first extension and the second extension in an overlapped configuration.

3. The protective liner of claim 1, wherein an overall length of the main collar portion, the first extension and the second extension is adjustably set in the joined configuration.

4. The protective liner of claim 3, wherein the overall length is altered to create an adjusted length by adjusting a position of the first extension with respect to a position of the second extension.

5. The protective liner of claim 4, wherein the adjusted length is maintained by the adjustable releasable fastener.

6. The protective liner of claim 1, wherein the collar is adjustable to accommodate a variety of sizes.

7. The protective liner of claim 1, wherein the adjustable releasable fastener comprises a hook element disposed on an interior surface of the first extension and a loop element disposed on an exterior surface of the second extension.

8. The protective liner of claim 1, wherein the adjustable releasable fastener comprises an adhesive element disposed on an interior surface of the first extension, wherein an exterior surface of the adhesive element is configured to join the exterior surface of the second extension.

9. The protective liner of claim 8, wherein the adhesive element comprises double-sided tape.

10. The protective liner of claim 1, wherein the material comprises spun-melt-spun (SMS) material.

11. The protective liner of claim 1, wherein the fluid repellent material comprises polypropylene and polyethylene laminate.

12. The protective liner of claim 1, wherein the material is coated with a fluid repellent.

13. The protective liner of claim 12, wherein the fluid repellent comprises polypropylene and polyethylene laminate.

14. The protective liner of claim 1, wherein the material is a soft, hypoallergenic, latex-free material.

15. The protective liner of claim 1, wherein the material is printable.

16. The protective liner of claim 1, wherein the material is pliable.

17. The protective liner of claim 1, wherein the material is selected from a variety of colors including medical blue, green, white, purple and orange.

18. The protective liner of claim 1, wherein the material is radiolucent.

19. The protective liner of claim 1, wherein the material is disposable.

20. The protective liner of claim 1, wherein the material is tear free.

21. The protective liner of claim 1, wherein the collar and chest portion of the protective liner form a unitary configuration.

22. The protective liner of claim 21, wherein the material comprises spun-melt-spun (SMS) material.

23. The protective liner of claim 22, wherein the material is coated with a fluid repellent.

24. The protective liner of claim 23, wherein the fluid repellent comprises polypropylene and polyethylene laminate.

25. The protective liner of claim 21, wherein the unitary configuration is stamped from a supply of material.

26. The protective liner of claim 25, wherein the supply of material comprises spun-melt-spun (SMS) material.

27. The protective liner of claim 26, wherein the SMS material is coated with a fluid repellent.

28. The protective liner of claim 27, wherein the fluid repellent comprises polypropylene and polyethylene laminate.

29. The protective liner of claim 21, wherein the unitary configuration is perforated along a supply of material.

30. The protective liner of claim 29, wherein the supply of material comprises spun-melt-spun (SMS) material.

31. The protective liner of claim 22, wherein the SMS material is coated with a fluid repellent.

32. The protective liner of claim 23, wherein the fluid repellent comprises polypropylene and polyethylene laminate.

33. The protective liner of claim 1, wherein each length of the first extension and the second extension is approximately 8.00 inches, an overall length of the first extension, the second extension and the main chest portion is approximately 24.00 inches, the thickness of the collar is approximately 3.00 inches, the length of the straight portion is approximately 5.00 inches, the width of the chest portion is approximately 8.00 inches, and the radius of the curved end portion is approximately 5.00 inches.

34. The protective liner of claim 1, wherein the protective coating comprises an interior surface and an exterior surface, and a slip-resistant material applied to the exterior surface.

35. The protective liner of claim 34, wherein the slip-resistant material is applied to selective portions of the exterior surface.

36. The protective liner of claim 34, wherein the slip-resistant material is applied to the entirety of the exterior surface.

37. The protective liner of claim 34, wherein the slip-resistant material is an adhesive and/or a tactile finish.

38. The protective liner of claim 37, wherein the slip-resistant material comprises double-sided tape.

39. The protective liner of claim 34, wherein the slip-resistant material is sufficiently applied to support and maintain a radiation shield in position.

40. A protective liner comprising:
a first material forming:
a collar comprising:
a main collar portion;
a first extension emanating from the main collar portion in a first direction;
a second extension emanating from the main collar portion in a second direction opposite to the first direction;
a chest portion extending from the main collar portion;
an adjustable releasable fastener for joining the first extension to the second extension, the adjustable releasable fastener disposed upon at least one of the first extension and second extension, wherein a material of the protective liner comprises a non-woven material; and
a second material coating a surface of the first material, wherein the second material is fluid repellent.

41. The protective liner of claim 40, wherein the first material comprises an interior surface and an exterior surface, and the second fluid repellent material coats the interior surface.

42. The protective liner of claim 40, wherein the first material comprises spun-melt-spun (SMS) material.

43. The protective liner of claim 40, wherein the second material comprises polypropylene and polyethylene laminate.

44. The protective liner of claim 40, wherein the collar and chest portion of the first material form a unitary configuration.

45. The protective liner of claim 44, wherein the unitary configuration is stamped from a supply of the first material.

46. The protective liner of claim 45, wherein the supply of first material comprises spun-melt-spun (SMS) material.

47. The protective liner of claim 46, wherein the second material comprises polypropylene and polyethylene laminate.

48. The protective liner of claim 44, wherein the unitary configuration is perforated along a supply of the first material.

49. The protective liner of claim 48, wherein the supply of the first material comprises spun-melt-spun (SMS) material.

50. The protective liner of claim 49, wherein the second material comprises polypropylene and polyethylene laminate.

51. The protective liner of claim 41, wherein a slip-resistant material is applied to the exterior surface of the first material.

52. The protective liner of claim 51, wherein the slip-resistant material is applied to selective portions of the exterior surface.

53. The protective liner of claim 51, wherein the slip-resistant material is applied to the entirety of the exterior surface.

54. The protective liner of claim 51, wherein the slip-resistant material is an adhesive and/or a tactile finish.

55. The protective liner of claim 54, wherein the slip-resistant material comprises double-sided tape.

56. The protective liner of claim 51, wherein the slip-resistant material is sufficiently applied to support and maintain a radiation shield in position.

57. A protective liner comprising:
a collar comprising:
a main collar portion;
a first extension emanating from the main collar portion in a first direction;
a second extension emanating from the main collar portion in a second direction opposite to the first direction;
a first tie extension extending from the first extension;
a second tie extension extending from the second extension; and
a chest portion extending from the main collar portion, wherein a material of the protective liner comprises a non-woven, fluid repellent material.

58. The protective liner of claim 57, wherein the first tie extension and the second tie extension join the a first extension and the second extension together.

59. The protective liner of claim 57, wherein an overall length of the main collar portion, the first extension and the second extension is adjustably set by joining the first tie extension to the second tie extension.

60. The protective liner of claim 59, wherein the overall length is altered to create an adjusted length by adjusting a position of the first extension with respect to a position of the second extension.

61. The protective liner of claim 57, wherein the collar is adjustable to accommodate a variety of sizes.

62. The protective liner of claim 57, wherein the material comprises spun-melt-spun (SMS) material.

63. The protective liner of claim 57, wherein the fluid repellent material comprises polypropylene and polyethylene laminate.

64. The protective liner of claim 57, wherein the material is coated with a fluid repellent.

65. The protective liner of claim 64, wherein the fluid repellent comprises polypropylene and polyethylene laminate.

66. The protective liner of claim 57, wherein the material is a soft, hypoallergenic, latex-free material.

67. The protective liner of claim 57, wherein the material is printable.

68. The protective liner of claim 57, wherein the material is pliable.

69. The protective liner of claim 57, wherein the material is selected from a variety of colors including medical blue, green, white, purple and orange.

70. The protective liner of claim 57, wherein the material is radiolucent.

71. The protective liner of claim 57, wherein the material is disposable.

72. The protective liner of claim 57, wherein the material is tear free.

73. The protective liner of claim 57, wherein the collar, the chest portion, the first tie extension and the second tie extension of the protective liner form a unitary configuration.

74. The protective liner of claim 73, wherein the material comprises spun-melt-spun (SMS) material.

75. The protective liner of claim 74, wherein the material is coated with a fluid repellent.

76. The protective liner of claim 75, wherein the fluid repellent comprises polypropylene and polyethylene laminate.

77. The protective liner of claim 73, wherein the unitary configuration is stamped from a supply of material.

78. The protective liner of claim 77, wherein the supply of material comprises spun-melt-spun (SMS) material.

79. The protective liner of claim 78, wherein the SMS material is coated with a fluid repellent.

80. The protective liner of claim 79, wherein the fluid repellent comprises polypropylene and polyethylene laminate.

81. The protective liner of claim 73, wherein the unitary configuration is perforated along a supply of material.

82. The protective liner of claim 81, wherein the supply of material comprises spun-melt-spun (SMS) material.

83. The protective liner of claim 82, wherein the SMS material is coated with a fluid repellent.

84. The protective liner of claim 83, wherein the fluid repellent comprises polypropylene and polyethylene laminate.

85. A protective liner comprising:
a first material forming:
  a collar comprising:
    a main collar portion;
    a first extension emanating from the main collar portion in a first direction;
    a second extension emanating from the main collar portion in a second direction opposite to the first direction;
    a first tie extension extending from the first extension;
    a second tie extension extending from the second extension;
  a chest portion extending from the main collar portion, wherein a material of the protective liner comprises a non-woven material; and
a second material coating a surface of the first material, wherein the second material is fluid repellent.

86. The protective liner of claim 85, wherein the first material comprises an interior surface and an exterior surface, and the second fluid repellent material coats the interior surface.

87. The protective liner of claim 85, wherein the first material comprises spun-melt-spun (SMS) material.

88. The protective liner of claim 85, wherein the second material comprises polypropylene and polyethylene laminate.

89. The protective liner of claim 85, wherein the collar and chest portion of the first material form a unitary configuration.

90. The protective liner of claim 89, wherein the unitary configuration is stamped from a supply of the first material.

91. The protective liner of claim 90, wherein the supply of first material comprises spun-melt-spun (SMS) material.

92. The protective liner of claim 91, wherein the second material comprises polypropylene and polyethylene laminate.

93. The protective liner of claim 89, wherein the unitary configuration is perforated along a supply of the first material.

94. The protective liner of claim 93, wherein the supply of the first material comprises spun-melt-spun (SMS) material.

95. The protective liner of claim 94, wherein the second material comprises polypropylene and polyethylene laminate.

96. The protective liner of claim 1, wherein the main collar portion covers a front region of a patient's neck.

97. The protective liner of claim 1, wherein the chest portion extends down a front region of a patient's chest.

98. The protective liner of claim 1, wherein the adjustable fastener is disposed at a dorsal region of a patient's neck.

99. The protective liner of claim 40, wherein the main collar portion covers a front region of a patient's neck.

100. The protective liner of claim 40, wherein the chest portion extends down a front region of a patient's chest.

101. The protective liner of claim 40, wherein the adjustable fastener is disposed at a dorsal region of a patient's neck.

102. The protective liner of claim 57, wherein the main collar portion covers a front region of a patient's neck.

103. The protective liner of claim 57, wherein the chest portion extends down a front region of a patient's chest.

104. The protective liner of claim 57, wherein the adjustable fastener is disposed at a dorsal region of a patient's neck.

105. The protective liner of claim 85, wherein the main collar portion covers a front region of a patient's neck.

106. The protective liner of claim 85, wherein the chest portion extends down a front region of a patient's chest.

107. The protective liner of claim 85, wherein the adjustable fastener is disposed at a dorsal region of a patient's neck.

108. The protective liner of claim 1 further comprising a radiation device attached to the material.

109. The protective liner of claim 108, wherein the radiation device comprises a dosimeter.

110. The protective liner of claim 40 further comprising a radiation device attached to the material of the protective liner.

111. The protective liner of claim 110, wherein the radiation device comprises a dosimeter.

112. The protective liner of claim 57 further comprising a radiation device attached to the material.

113. The protective liner of claim 112, wherein the radiation device comprises a dosimeter.

114. The protective liner of claim 85 further comprising a radiation device attached to the material of the protective liner.

115. The protective liner of claim 114, wherein the radiation device comprises a dosimeter.

116. The protective liner of claim 1, wherein the chest portion extends downwardly from and substantially perpendicular to the main collar portion.

117. The protective liner of claim 40, wherein the chest portion extends downwardly from and substantially perpendicular to the main collar portion.

118. The protective liner of claim 57, wherein the chest portion extends downwardly from and substantially perpendicular to the main collar portion.

119. The protective liner of claim 85, wherein the chest portion extends downwardly from and substantially perpendicular to the main collar portion.

* * * * *